(12) United States Patent
Sanghani et al.

(10) Patent No.: US 9,951,356 B2
(45) Date of Patent: Apr. 24, 2018

(54) PROCESSES TO PREPARE ELONGATED 2-KETOACIDS AND C6-C10 COMPOUNDS THEREFROM VIA GENETIC MODIFICATIONS TO MICROBIAL METABOLIC PATHWAYS

(71) Applicant: Dow Global Technologies LLC, Midland, MI (US)

(72) Inventors: Paresh C. Sanghani, Carmel, IN (US); Brandon A. Rodriguez, Houston, TX (US); Christopher C. Stowers, Carmel, IN (US); Amudhan Venkateswaran, Zionsville, IN (US)

(73) Assignee: Dow Global Technologies LLC, Midland, MI (US)

( * ) Notice: Subject to any disclaimer, the term of this patent is extended or adjusted under 35 U.S.C. 154(b) by 31 days.

(21) Appl. No.: 15/030,616

(22) PCT Filed: Dec. 10, 2014

(86) PCT No.: PCT/US2014/069438
§ 371 (c)(1),
(2) Date: Apr. 20, 2016

(87) PCT Pub. No.: WO2015/089127
PCT Pub. Date: Jun. 18, 2015

(65) Prior Publication Data
US 2016/0355850 A1 Dec. 8, 2016

Related U.S. Application Data

(60) Provisional application No. 61/915,040, filed on Dec. 12, 2013.

(51) Int. Cl.
*C12P 7/64* (2006.01)
*C12P 7/24* (2006.01)
(Continued)

(52) U.S. Cl.
CPC .............. *C12P 7/6409* (2013.01); *C12N 1/14* (2013.01); *C12N 1/20* (2013.01); *C12N 9/0006* (2013.01);
(Continued)

(58) Field of Classification Search
None
See application file for complete search history.

(56) References Cited

U.S. PATENT DOCUMENTS 8,232,089 B2 7/2012 Urano et al.
8,298,798 B2 10/2012 Liao et al.
(Continued)

FOREIGN PATENT DOCUMENTS

WO 2009046375 A2 4/2009
WO 2009096370 A1 8/2009
(Continued)

OTHER PUBLICATIONS

International Search Report and Written Opinion dated Mar. 18, 2015 pertaining to International Application No. PCT/US2014/069438.
(Continued)

*Primary Examiner* — Robert B Mondesi
*Assistant Examiner* — Richard C Ekstrom
(74) *Attorney, Agent, or Firm* — Dinsmore & Shohl LLP

(57) ABSTRACT

Modification of metabolic pathways includes genetically engineering at least one enzyme involved in elongating 2-ketoacids during leucine biosynthesis, and preferably at least isopropylmalate dehydrogenase or synthase (LeuB or LeuA in *E. coli*), to include at least such non-native enzyme, enzyme complex, or combination thereof to convert 2-ketobutyrate or 2-ketoisovalerate to a C7-C11 2-ketoacid, wherein the production of such is at a higher efficiency than if a purely native pathway is followed. The C7-C11 2-ke-
(Continued)

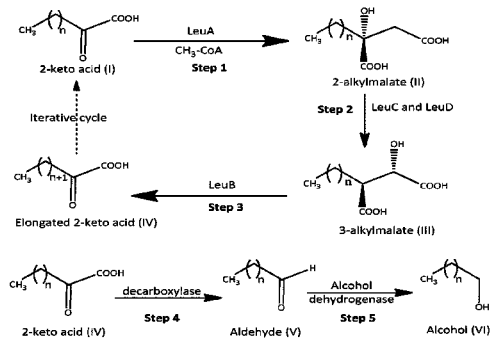

Figure 1:
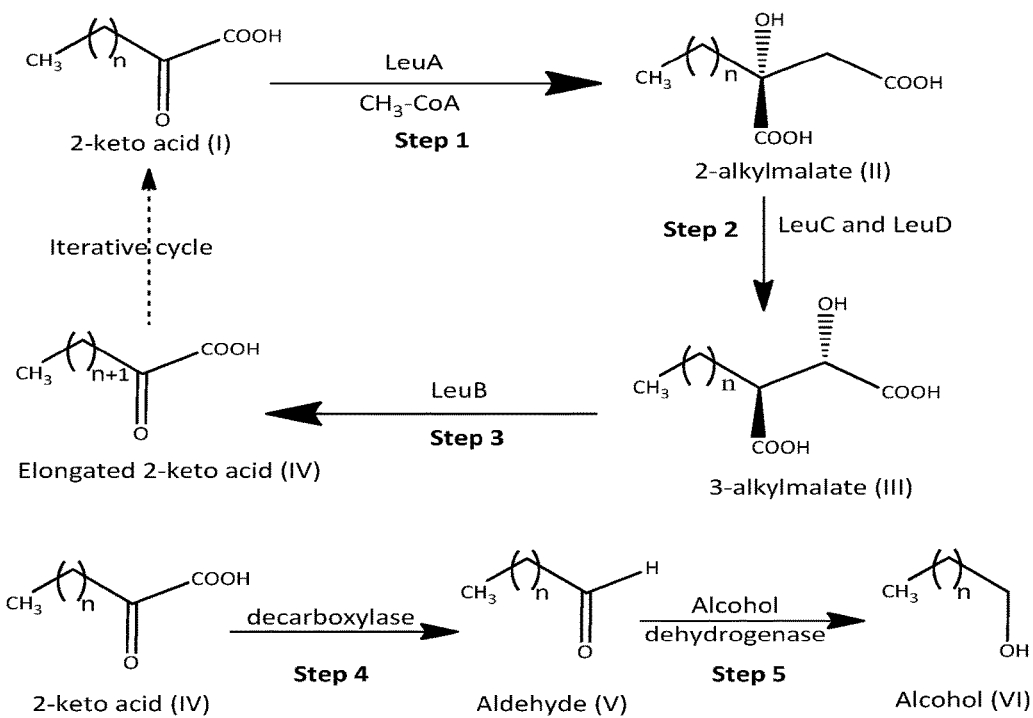

Elongation of 2-ketoacids by recursive activities of LeuA,B,C,D (steps 1-3) and the conversion of the elongated 2-ketoacid to alcohol through the activities of a thiamin dependent decarboxylase and an alcohol dehydrogenase (step 4-5).

toacid may then be converted, via a native or genetically engineered thiamin dependent decarboxylase, to form a C6-C10 aldehyde having one less carbon than the C7-C11 2-ketoacid being converted. In some embodiments the C6-C10 aldehyde may then be converted via additional native or genetically engineered enzymes to form other C6-C10 products, including alcohols, carboxylic acids, and alkanes. This genetic engineering offers the opportunity for commercial scale of in vivo biosynthetic processes that may be more cost-efficient than non-biobased approaches to produce the same products.

14 Claims, 2 Drawing Sheets

(51) Int. Cl.
    *C12P 7/26*     (2006.01)
    *C12P 7/40*     (2006.01)
    *C12N 9/04*     (2006.01)
    *C12N 1/20*     (2006.01)
    *C12N 1/14*     (2006.01)
    *C12N 9/10*     (2006.01)
    *C12N 9/88*     (2006.01)
    *C12N 15/52*     (2006.01)

(52) U.S. Cl.
    CPC ............ *C12N 9/1025* (2013.01); *C12N 9/88* (2013.01); *C12N 15/52* (2013.01); *C12P 7/24* (2013.01); *C12P 7/26* (2013.01); *C12P 7/40* (2013.01); *C12Y 101/01085* (2013.01); *C12Y 203/03013* (2013.01); *C12Y 402/01033* (2013.01)

(56) References Cited

U.S. PATENT DOCUMENTS

2011/0201083 A1* 8/2011 Liao ............... C12N 9/1022 435/193
2012/0070868 A1* 3/2012 Lee ............... C12N 9/0006 435/134
2014/0377857 A1* 12/2014 Liao ............... C12M 21/12 435/297.1

FOREIGN PATENT DOCUMENTS

WO     2010045629 A2     4/2010
WO     2012135731 A2     10/2012
WO     2016094604 A1     6/2016

OTHER PUBLICATIONS

Felnagle et al., "Engineering Synthetic Recursive Pathways to Generate Non-Natural Small Molecules", Nature Chemical Biology, Jun. 2012, 518-526, vol. 8, Nature America, Inc.
Han et al., "Sites and Mechanisms of Aconitase Inactivation by Peroxynitrite: Modulation by Citrate and Glutathione", Biochemistry, 2005, 11986-11996, 44, American Chemical Society.
Hsu et al., "Leucine Biosynthesis in *Saccharomyces cerevisiae*, Purification and Characterization of b-Isopropylmalate Dehydrogenase", The Journal of Biological Chemistry, 1980, 7255-7260, vol. 255 No. 15.
Imada et al., "Structure of 3-Isopropylmalate Dehydrogenase in Complex with 3-Isopropylmalate at 2.0 A Resolution: the Role of Glu88 in the Unique Substrate-Recognition Mechanism", Structure, Aug. 1998, 971-982, 6, Current Biology Publications ISSN 0969-2126.

Lee et al., "Metabolic Engineering of Clostridium Acetobutylicum M5 for Highly Selective Butanol Production", Biotechnology Journal, 2009, 1432-1440, 4, Wiley-VCH Verlag GmbH & Co.
Marcheschi et al., "A Synthetic Recursive '+1' Pathway for Carbon Chain Elongation", ACS Chemical Biology, 2012, 689-697, 7, American Chemical Society.
Sanghani et al., "Kinetic Mechanism of Human Glutathione-Dependent Formaldehyde Dehydrogenase", Biochemistry, 2000, 10720-10729, 39, American Chemical Society.
Shen et al., "A Synthetic Iterative Pathway for Ketoacid Elongation", Methods in Enzymology, 2011, 469-481, 497, Elsevier Inc.
Wang et al., "Optimization of Butanol Production from Tropical Maize Stalk Juice by Fermentation with Clostridium Beijerinckii NCIMB 8052", Bioresource Technology, 2011, 9985-9990, 102, Elsevier Ltd.
Zhang et al., "Expanding Metabolism for Biosynthesis of Nonnatural Alcohols", PNAS, Dec. 2008, 20653-20658, vol. 105 No. 52, The National Academy of Science of the USA.
Atsumi et al., "Non-Fermentative Pathways for Synthesis of Branched-Chain Higher Alcohols as Biofuels", Nature, 2008, vol. 451, 86-90, Nature Publishing Group.
Becker et al., "Bio-Based Production of Chemicals, Materials and Fuels—Corynebacterium Glutamicum as Versatile Cell Factory", Current Opinion in Biotechnology, 2012, 23, 631-640, Elsevier.
Becker et al., "Systems and Synthetic Metabolic Engineering for Amino Acid Production—The Heartbeat of Industrial Strain Development", Current Opinion in Biotechnology, 2012, 23, 718-726, Elsevier.
Choi et al., "Microbial Production of Short-Chain Alkanes", Nature, 2013, 502, 571-576, Macmillan Publishers.
Datsenko et al., "One-Step Inactivation of Chromosomal Genes in *Escherichia coli* K-12 Using PCR Products", Proc. Natl. Acad. Sci. USA, 2000, 97:12, 6640-6645.
Gronenberg et al., "Next Generation Biofuel Engineering in Prokaryotes", Current Opinion in Biotechnology, 2013, 17, 462-471, Elsevier.
Holton et al., "Structural Characterization of a D-Isomer Specific 2-Hydroxyacid Dehydrogenase from *Lactobacillus delbrueckii* ssp. *bulgaricus*", Journal of Structural Biology, 2013, 181, 179-184, Elsevier Inc.
Hummel, Werner, "Large-Scale Applications of NAD(P)-Dependent Oxidoreductases: Recent Developments", Tibtech, 1999, 17, 487-492, Elsevier Science Ltd.
Koon et al., "Crystal Structure of LeuA from *Mycobacterium tuberculosis*, a Key Enzyme in Leucine Biosynthesis", Proc. Natl. Acad. Sci. USA, 2004, 101:22, 8295-8300.
Manikandan et al., "Structural Studies on the Enzyme Complex Isopropylmalate Isomerase [LeuCD] from *Mycobacterium tuberculosis*", Proteins, 2010, 35-49, Wiley-Liss, Inc.
Spaepen et al., "Characterization of Phenylpyruvate Decarboxylase, Involved in Auxin Production of Azospirillum Brasilense", Journal of Bacteriology, 2007, 189:21, 7626-7633.
Vedha-Peters et al., "Creation of a Broad-Range and Highly Stereoselective D-Amino Acid Dehydrogenase for the One-Step Synthesis of D-Amino Acids", J. Am. Chem. Soc., 2006, 128, 10923-10929, American Chemical Society.
Versees et al., "The Crystal Structure of Phenylpyruvate Decarboxylase from Azospirillum Brasilense at 1.5 A Resolution Implications for its Catalytic and Regulatory Mechanism", The FEBS Journal, 2007, 274, 2363-2375, The Authors Journal compilation.
Xiong et al., "A Bio-Catalytic Approach to Aliphatic Ketones", Scientific Reports, 2:311, doi: 10.1035/srep0311, (2012).
Zhang et al., "A Synthetic Metabolic Pathway for Production of the Platform Chemical Isobutyric Acid", ChemSusChem, 2011, 4, 1068-1070 Wiley-VCH Verlag GmbH & Co.
International Search Report and Written Opinion pertaining to PCT/US2015/064879 dated Mar. 22, 2016.
International Search Report and Written Opinion pertaining to PCT/US2016/069430 dated Jul. 4, 2017.
International Search Report and Written Opinion pertaining to PCT/US2016/069476 dated Jul. 4, 2017.

(56) References Cited

OTHER PUBLICATIONS

Rude et al., "New Microbial Fuels: A Biotech Perspective", Current Opinion in Microbiology, 2009, 274-281.

Zhang et al., "Subdomain II of alpha-isopropylmalate synthase is essential for activity: inferring a mechanism of feedback inhibition", The Journal of biological chemistry 2014, 289, 27966-27978.

\* cited by examiner

Elongation of 2-ketoacids by recursive activities of LeuA,B,C,D (steps 1-3) and the conversion of the elongated 2-ketoacid to alcohol through the activities of a thiamin dependent decarboxylase and an alcohol dehydrogenase (step 4-5).

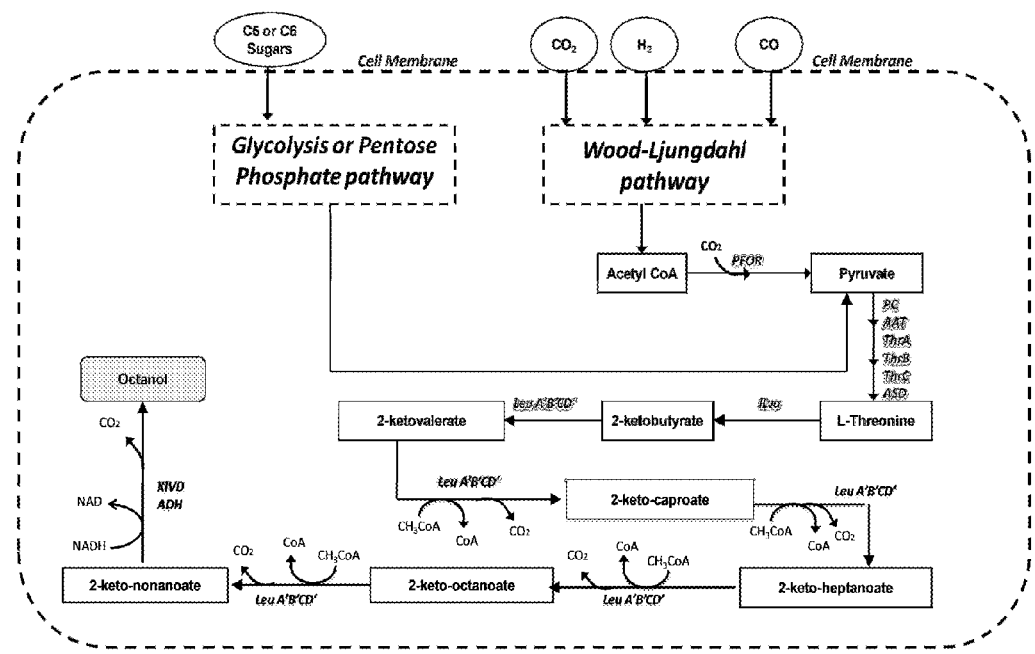

Key: PFOR – Pyruvate:ferredoxin-oxidoreductase; PC-pyruvate carboxylase; AAT-Aspartate aminotransferase; ThrA-Bifunctional aspatokinase serine dehydrogenase; ThrB-homoserine kinase; ThrC-threonine synthase; ASD-Aspartate semialdehyde dehydrogenase; Ilva-threonine deaminase; Leu A'B'CD'-modified forms of LeuA, LeuB, LeuCD complex; KIVD - ketoisovalerate decarboxylase (a thiamin dependent decarboxylase); ADH - alcohol dehydrogenase.

FIGURE 2

PROCESSES TO PREPARE ELONGATED 2-KETOACIDS AND C6-C10 COMPOUNDS THEREFROM VIA GENETIC MODIFICATIONS TO MICROBIAL METABOLIC PATHWAYS

CROSS-REFERENCE TO A RELATED APPLICATION

The present application claims the benefit of U.S. Provisional Patent Application Ser. No. 61/915,040, filed Dec. 12, 2013, entitled "Process to Prepare Octanol From Syngas Via Genetic Modifications to Microbial Metabolic Pathways," which is incorporated herein by reference in its entirety.

The invention relates to the field of using biological enzymes to produce C6-C10 aldehydes and products made therefrom. More particularly, it relates to the field of using engineered enzymes that can be either expressed by a genetically-modified microbial organism to convert a suitable substrate to a C6-C10 aldehyde via one or more metabolic pathways, or can be incubated in vitro to convert 2-ketobutyrate or 2-ketoisovalerate to an elongated 2-ketoacid and then to convert the 2-ketoacid to a C6-C10 aldehyde.

Concerns about the future scarcity, cost, and environmental impact of obtaining and using fossil fuels have stimulated interest in the exploitation of cheap, renewable biomass as alternative sources for both fuels and chemicals made from them. As crude oil prices have risen, biobased chemicals and industrial products have become attractive alternatives to their petroleum-derived counterparts. Fermentation processes using anaerobic microbial organisms offer a promising path for converting biomass and agricultural wastes into useful products, while at the same time remediating problems that may be encountered in disposal of low-value agricultural commodities and food processing byproducts/wastes. Some of the useful products that can be prepared from low-cost biomass feedstocks are organic acids and alcohols, including in particular C6-C10 alcohols such as octanol. Octanol finds particular use as a lower-cost starting material to prepare octene, which is a highly desirable feedstock chemical in a number of industries. These industries include the polyethylene industry, which uses octene as a co-monomer for solution polymerizations, and the detergent industry, which uses it to alkylate phenols to produce detergent precursors. Octene has been typically prepared by linear alpha olefin (LAO) technology which relies on energy-intensive tetramerization, and as a result, octene supplies are often insufficient, contributing to undesirable fluctuations in its price. Thus, identification of better and less expensive methods to produce octanol would be expected to lead to less expensive production of octene. In general, use of fermentation processes to produce octanol could provide such cost reduction, which would in turn increase supply and stabilize the price of octene.

In general methods for the improvement of industrial microbial organisms range from the random approach of classical strain improvement (CSI) to the highly rational methods of metabolic engineering. CSI is often effective for alleviating product inhibition or improving productivity, but is a far less effective approach to generate strains capable of producing entirely new products. Furthermore, CSI is intensive as to both time and resources. This is because, in order to obtain strains with high tolerance to inhibitory fermentation products, it is necessary to continuously screen and select mutants by successively culturing the strain in the media in the presence of increasing inhibitor concentrations. This is usually carried out in conjunction with induced mutagenesis using chemical mutagens and/or ultraviolet (UV) radiation. However, the conventional culture screening process is generally tedious, time-consuming, and often fruitless.

Metabolic modifications are frequently more effective at creating strains that produce new products. This is because genes, and in some cases even entire pathways, can be transferred between organisms (recombinant methods), and/or enzymes can be modified (engineered methods). These methods avoid some of the disadvantages of CSI. Metabolic engineering, a term comprehending both recombinant and engineered methods, is a targeted and often faster approach that is widely used to design strains to achieve higher efficiencies in metabolite overproduction, through alterations in the metabolic flux distribution. Most of this work to date is related to the production of secondary metabolites (such as antibiotics), amino acids (e.g., lysine), and heterologous proteins, using organisms with well-studied genetics and physiology (e.g., *E. coli*, yeast, and hybridoma cells). Stoichiometric analysis of metabolic flux distributions provides a guide to appropriate metabolic modification, optimal medium formulation and feeding strategies, and bioprocess optimization. However, this approach still requires in-depth knowledge of the metabolic and regulatory networks in the fermentation cells. Although these rational approaches have been successful in cases involving a single gene or a few genes within a single gene cluster, they have often been ineffective in cases involving more complex or largely unknown metabolic pathways. This is because such approaches usually target one gene at a time, and thus fail to predict complex interactions among multiple genes in a given pathway.

Enzyme modification is performed by modifying that portion of the genetic code, i.e., the organism's DNA, which corresponds to the expression of that enzyme. Modification of enzymes can lead to entirely new functionality or may be used to improve the specificity or efficiency of desired intermediates or products. Additionally, certain enzymes are known to be promiscuous, often performing tasks beyond their known natural roles. Such enzymes may also be modified to perform novel conversions, but to date the success of this approach has frequently been limited to product yields that are not commercially viable. See, e.g., Zhang, K.; Sawaya, M. R.; Eisenberg, D. S.; Liao, J. C. "Expanding metabolism for biosynthesis of nonnatural alcohols," *Proc. Natl. Acad. Sci. USA*, 2008, 105:20653-20658. Modifying multiple enzymes in a pathway may theoretically be used as a technique to maximize specificity and/or catalytic efficiency.

One example of an organism known to produce octanol under certain conditions is *Clostridium*. Various species of *Clostridium* (e.g., *C. acetobutylicum*, *difficile*, and *kluyveri*) are employed in WO2012135731. That publication ascribes a *Clostridium* species' poorly selective production, that includes a small amount of n-octanol, among other products, to the engineered microbial organism's ability to express or overexpress beta-ketothiolase (e.g., BktB), acetyl CoA acetyltransferase (e.g., AtoB), 3-hydroxybutyryl-CoA dehydrogenase (e.g., Hbd, from the *Clostridium*, or PaaHl), crotonase (e.g., Crt), and trans-enoyl-CoA reductase (e.g., Ter). These modifications are generally to the organism's CoA pathway for the production of higher alcohols. This pathway avoids the butanol production pathway found in many species of *Clostridium*, which involves oxygen-sensitive enzymes and intermediates. However, the amount of n-octanol produced via this invention is too small to be commercially viable. See also, e.g., Lee, J. Y.; Jang, Y. S.; Lee, J.; Papoutsakis, E. T.; Lee, S. Y. "Metabolic engineering of *Clostridium acetobutylicum* M5 for highly selective butanol production," *Biotechnol.*, 2009, 4:1432-1440; and Wang, Y.; Blaschek, H. P. "Optimization of butanol production from tropical maize stalk juice by fermentation with *Clostridium beijerinckii*," *Bioresour. Technol.*, 2011, 102, 9985-9990.

In one embodiment, the invention provides a process for preparing a C7-C11 2-ketoacid comprising contacting a substrate, selected from 2-ketobutyrate and 2-ketoisovalerate, and (1) a native or genetically modified LeuA enzyme; (2) a genetically modified LeuB' enzyme, wherein the enzyme is (a) obtained from *Escherichia coli* and has an amino acid sequence corresponding to Sequence Listing, SEQ ID 2; the enzyme having been modified in that alanine, glycine, valine or leucine is independently substituted for Leu-96, Val-198, or a combination thereof; or (b) the enzyme has an amino acid sequence that is at least 60 percent homologous to the amino acid sequence of Sequence Listing, SEQ ID 2; the enzyme having been modified as in (a); and (3) a native or genetically modified LeuCD' enzyme complex; under conditions such that the 2-ketobutyrate or 2-ketoisovalerate is converted, via one or more steps, to a C7-C11 2-ketoacid.

In another embodiment, the C7-C11 2-ketoacid produced as described in the previous paragraph is contacted with a native or genetically modified thiamin dependent decarboxylase, under conditions such that the C7-C11 2-ketoacid is converted to a C6-C10 aldehyde having one less carbon atom than the C7-C11 2-ketoacid being converted.

In still another embodiment, the invention provides a microbial organism that expresses or overexpresses an enzyme that is (1) obtained from *Escherichia coli* and has an amino acid sequence corresponding to Sequence Listing, SEQ ID 2; the enzyme having been modified in that alanine, glycine, valine or leucine is independently substituted for Leu-96, Val-198, or a combination thereof; or (2) has an amino acid sequence that is at least 60 percent homologous to the amino acid sequence of Sequence Listing, SEQ ID 2; the enzyme having been modified as in (1).

In yet another embodiment the invention provides a process to prepare a C6-C10 aldehyde comprising (1) contacting a carbon-containing substrate and one or more native or genetically modified enzymes under conditions to form 2-ketobutyrate or 2-ketoisovalerate; (2) contacting the 2-ketobutyrate or 2-ketoisovalerate and (a) a native or genetically modified LeuA enzyme; (b) a genetically modified LeuB' enzyme, wherein the enzyme is (i) obtained from *Escherichia coli* and has an amino acid sequence corresponding to Sequence Listing, SEQ ID 2; the enzyme having been modified in that alanine, glycine, valine or leucine is independently substituted for Leu-96, Val-198, or a combination thereof; or (ii) the enzyme has an amino acid sequence that is at least 60 percent homologous to the amino acid sequence of Sequence Listing, SEQ ID 2; the enzyme having been modified as in (a); and (c) a native or genetically modified LeuCD' enzyme complex; under conditions such that the 2-ketobutyrate or 2-keto-isovalerate is converted, via one or more steps, to a C7-C11 2-ketoacid; and (3) contacting the C7-C11 2-ketoacid and a native or genetically modified thiamin dependent decarboxylase under conditions such that the C7-C11 2-ketoacid is converted to a C6-C10 aldehyde having one less carbon atom than the C7-C11 2-ketoacid being converted; each of (1), (2) and (3) occurring in one or more steps; wherein (1), (2) and (3) independently occur within or outside of a genetically modified microbial organism.

FIG. 1 shows the elongation of a 2-ketoacid by the recursive activities of LeuABCD, in steps 1 to 3. Following the elongation, the resulting elongated 2-ketoacid (IV) is then converted to an aldehyde (V), via the activity of a (thiamin dependent) decarboxylase in step 4, and finally to an alcohol (VI), via the activity of an alcohol dehydrogenase in step 5.

FIG. 2 shows two related but different routes to produce 1-octanol. In one, a Wood-Ljungdahl pathway converts synthesis gas to acetyl CoA, and another pathway then converts the acetyl CoA to pyruvate. The pyruvate is then converted to 2-ketobutyrate, and finally a LeuABCD pathway is initiated, wherein the 2-ketobutyrate is converted to (in this embodiment) 2-ketononanoate. Once the elongated 2-ketoacid has been formed (the 2-ketononanoate), a (thiamin dependent) decarboxylase converts it to a C6-C10 aldehyde (in this embodiment, octanal), and an alcohol dehydrogenase converts the octanal to a C6-C10 alcohol (in this embodiment, 1-octanol).

In the other route, also illustrated in FIG. 2, one of the potential sugar catabolism pathways, which in this embodiment is a glycolysis or pentose phosphate pathway, converts a C5 or C6 sugar to pyruvate, and thereafter the same pathway sequence is followed as in the first route to reach the 1-octanol.

SEQUENCE LISTING, SEQ ID 1, shows a native (wild type) *E. coli* LeuB gene sequence, with both base pairs and the corresponding amino acids. Sequence Listing Free Text states as follows: "Wild type *E. coli* LeuB."

SEQUENCE LISTING, SEQ ID 2, show the amino acids for the native (wild type) *E. coli* LeuB, but without the corresponding base pairs.

SEQUENCE LISTINGS, SEQ ID 3-20, show LeuB' variant enzymes with specific base pair modifications (shown in odd-numbered sequences) and amino acid modifications (without corresponding base pairs) (shown in even-numbered sequences), as described. Sequence Listing Free Text (<223>) for each states the designation of the particular variant. The designations are defined and discussed in the text hereinafter.

In general the present invention includes a process to convert 2-ketobutyrate or 2-keto-isovalerate to a C7-C11 2-ketoacid; a genetically modified enzyme or combination of enzymes to carry out that conversion; and a process to prepare a C6-C10 product, which may be an aldehyde, an alcohol, a carboxylic acid, or an alkane, via contact between a carbon-containing substrate, such as, for example, synthesis gas (syngas) or a C5 or C6 sugar, such as sucrose, glucose, or pentose, and a series of enzymes that convert the carbon-containing substrate to the C6-C10 product via one or more steps, and in certain embodiments via three or more steps, and preferably five or more steps. Either process may be carried out biosynthetically, in one of the described embodiments of a non-naturally occurring, i.e., genetically engineered, cell, i.e., in a non-naturally occurring microbial organism; or via in vitro methodology.

In the process to prepare a C6-C10 aldehyde, a selected carbon-containing substrate is converted first to pyruvate, and from pyruvate to either 2-ketobutyrate or, alternatively, to 2-ketoisovalerate, via the action of one or more enzymes and in one or more steps. The 2-ketobutyrate or 2-ketoisovalerate is then converted, via chain elongation, to a C7-C11 2-ketoacid, by means of the action of at least one of three non-native, i.e., genetically modified, enzymes or enzyme complexes or a combination thereof in the LeuABCD pathway (as it is termed with respect to the *E. coli* microbial organism), which is a portion of the non-natural leucine pathway (FIG. 1). The first group of potentially employed modified enzymes accomplishing this chain elongation are identified herein as constituting Leu A' (2-isopropylmalate synthase), Leu B' (isopropylmalate dehydrogenase), and Leu CD' (two enzymes that, together, are termed isopropylmalate isomerase complex). The C7-C11 2-ketoacid may then be converted to a C6-C10 aldehyde by the action of at least one more enzyme, including a native or genetically modified thiamin dependent decarboxylase, which converts the C7-C11 2-ketoacid to a C6-C10 aldehyde having one less carbon atom than the C7-C11 2-ketoacid being converted.

Finally, the C6-C10 aldehyde may be used as is, in a variety of industrial applications, or may be employed as an intermediate or starting material for production of other chemicals. For example, the C6-C10 aldehyde may be contacted with an alcohol dehydrogenase, which converts the C6-C10 aldehyde to the corresponding C6-C10 alcohol. Alternatively, it may be contacted with an aldehyde dehydrogenase, which converts it to the corresponding C6-C10 carboxylic acid. Finally, it may be contacted with a fatty aldehyde decarbonylase, which converts it to the corresponding C6-C10 alkane. Each of the thiamin dependent decarboxylase and the alcohol dehydrogenase, aldehyde dehydrogenase, or fatty aldehyde decarbonylase may independently be native or genetically modified.

The terms "genetically modified," or "modified," as used herein, refers to an enzyme (whether generally or a specifically named enzyme, e.g., alcohol dehydrogenase, etc.) having an intentionally altered amino acid sequence, or a microbial organism (depending upon placement of either term as an adjective) having an intentionally altered genome. Such alteration may have been accomplished via recombinant technology, where one or more genes are transferred from a second, different microbial organism into a target microbial organism; engineered technology, wherein the amino acids within the target microbial organism are altered, generally via site-directed mutagenesis, resulting in the conversion of at least one amino acid (and frequently more than one) to a different amino acid; or both.

In preferred embodiments the C6-C10 product, for example, a C6-C10 alcohol such as 1-octanol, is produced with desirably high specificity, i.e., preferably at least 25 percent (%), more preferably at least 40%, still more preferably at least 50%, and most preferably at least 70%, based on weight (wt) of total product (i.e., wt %), is the targeted product. Another way of stating this is that the yield of desired product (e.g., 1-octanol) is preferably at least 0.25 gram product per gram of feedstock (g/g), more preferably at least 0.4 g/g, still more preferably at least 0.5 g/g, and most preferably at least 0.7 g/g.

As noted hereinabove, the invention may be carried out either in vivo or in vitro. An in vivo approach may be preferred for commercial scale production, while an in vitro approach may be more convenient for laboratory and general research purposes, such as to carry out enzymatic assays. In general the in vivo approach employs a microbial organism's native metabolic pathway(s), first to convert a suitable carbon-containing substrate to pyruvate, and then to convert the pyruvate to 2-ketobutyrate or, alternatively, to 2-ketoisovalerate, in a varying number of steps.

In one embodiment, the selected microbial organism may possess a Wood-Ljungdahl pathway, also known as a "synthesis (syngas) fixation pathway," wherein syngas is converted to acetyl CoA. Such may be carried out effectively by certain acetate-producing bacteria species, such as those of the genus *Clostridium*, including but not limited to, in particular, *Clostridium ljungdahlii* (*C. ljungdahlii*). In this pathway, conversion of the syngas to acetyl CoA generally includes reduction of carbon dioxide to carbon monoxide, and then to acetyl CoA via the action of two enzymes, i.e., carbon monoxide dehydrogenase, which catalyzes the reduction of the carbon dioxide, and acetyl CoA synthase, which combines the resulting carbon monoxide with a methyl group to form acetyl CoA. From this point the acetyl CoA continues on another pathway wherein it is converted to pyruvate, via reduction by PFOR (ferredoxin oxidoreductase). Such pathways may be present in organisms including, for example, *Clostridium*, *Escherichia coli* (*E. coli*), *Azospirillum*, *Bacillus*, *Saccharomyces* and *Corynebacterium*.

In an alternative embodiment, a suitable (non-syngas) carbon-containing substrate, such as a C5 or C6 sugar (glucose, sucrose, pentose, or a combination thereof), may be converted directly to pyruvate via one of the sugar catabolism pathways, such as a glycolysis or pentose phosphate pathway.

Thereafter the pyruvate may be converted first to L-threonine, via PC (pyruvate carboxylase); AAT (aspartate aminotransferase); ThrABC (ThrA, which is a bifunctional aspartokinase/homoserine dehydrogenase); ThrB, which is homoserine kinase; and ThrC, which is threonine synthase); and ASD (aspartate semialdehyde dehydrogenase). The L-threonine is then converted to 2-ketobutyrate via ILva (threonine dehydratase). In an alternative embodiment, the pyruvate may be converted to 2-ketoisovalerate via the activities of IlvBN/IlvGM, IlvC, and IlvD. See, also, Zhang, K.; Sawaya, M. R.; et al., ibid.

Following production of 2-ketobutyrate or 2-ketoisovalerate, genetic modification of the native LeuABCD portion of the non-natural leucine biosynthesis pathway operates to effect conversion to a C7-C11 2-ketoacid via one or more steps. In certain embodiments several steps are involved and employ, in an in vivo approach, at least one modified (endogenous or exogenous) enzyme, enzyme complex, or combination thereof (collectively referred to herein as "LeuA'B'CD'"), to convert 2-ketobutyrate or 2-ketoisovalerate to a desired C7-C11 2-ketoacid. For example, 2-ketobutyrate is converted first to 2-ketovalerate, then to 2-ketocaproate, then to 2-ketoheptanoate or up to 2-ketoundecanoate, depending upon the desired final product, as chain-lengthening occurs. Alternatively, 2-ketoisovalerate is converted first to 2-ketoisocaproate, then to 2-ketoisoheptanoate, and so forth. However, it is optionally possible to modify only one enzyme, enzyme complex or combination thereof—for example, LeuA', LeuB', or LeuCD'—to obtain acceptable or desirable production of a C7-C11 2-ketoacid beginning with 2-ketobutyrate or 2-ketoisovalerate.

Once an elongated C7-C11 2-ketoacid is formed, such may be used as is, or converted to a C6-C10 aldehyde. For such conversion, a native or genetically modified thiamin dependent decarboxylase (DC') is employed, resulting in a C6-C10 aldehyde having one less carbon atom than the C7-C11 2-ketoacid being converted. C6-C10 aldehydes enjoy wide applicability both in themselves and as starting or intermediates in producing C6-C10 alcohols, carboxylic acids, alkanes, and combinations thereof, as described hereinabove. Production of a C6-C10 alcohol, in one embodiment, octanol, is illustrated in FIG. 1.

In order to enable a non-native organism to carry out some portion of the conversions in vivo as defined hereinabove, for example, to produce the C6-C10 aldehydes and/or C6-C10 alcohols, it is desirable to perform protocols similar to that described hereunder. In general the Examples included herewith involve enzyme engineering to alter the amino acids in order to modify enzyme functionality, particularly in terms of activity and/or specificity. This alteration in the amino acids may be used to produce modified enzyme for small scale purposes, for example, for in vitro assays; or may be the basis for genome modification in order to produce a strain of microbial organisms suitable for larger scale production.

The methodology may be carried out as is well understood by those skilled in the art. In general, a suitable database, such as GenBank, is used to obtain the genetic codes for the native enzyme(s), followed by identification of the codons suitable for modification. This identification may be used as the basis for art-known methods of protein engineering, wherein computer molecular modeling identifies and also enables differentiation of structural locations at which modifications of enzyme/substrate interfaces may be effectively employed. A given desirable modification is then performed, using a molecular biology technique called site-directed mutagenesis. The modified gene is then cloned into a replicative plasmid vector which, when transformed into a host microbial organism such as E. coli, enables the production of enzymes having a higher-than-native catalytic efficiency. The E. coli cells containing the targeted variant enzyme also produce other native proteins and, therefore, the variant-type enzymes must then be subjected to purification to separate out non-targeted proteins and general cell structures, leaving a purified enzyme that will exhibit a higher-than-native, i.e., higher than wild type, catalytic efficiency. This can be appropriately assayed in vitro, according to the methodology most suited to the given particular enzyme. An assayed enzyme that is shown to have a desirable level of catalytic efficiency is thereby confirmed to be the product of a desirable genetic modification, and may be used for in vitro production methods, such as for the in vitro production of a given C7-C11 2-ketoacid, such as 2-ketononanoate, and/or a C6-C10 aldehyde, such as octanal, and/or a product made from the C6-C10 aldehyde, such as a C6-C10 alcohol, carboxylic acid, or alkane.

A particular application for the above-described methodology is to produce a desirable organism for large or otherwise commercial scale fermentative production of an enzyme-facilitated product, such as a C6-C10 aldehyde or one of the C6-C10 products that may be prepared therefrom. Such preparation may be carried out by inserting the DNA, or pieces of DNA, which encode for the desired improved enzyme into the genome of a second microbial organism known or believed to possess other desirable characteristics, such as, for example, capability to resist inhibitors during fermentation, capability to produce pyruvate (or acetyl CoA) from a particular carbon-containing substrate, or some other advantageous trait(s). Thus, the second microbial organism is now genetically-modified, in that it produces a genetically modified enzyme.

In another embodiment, it is also possible to simply identify a microbial organism having native enzymes that are useful in a desired overall pathway, and either use that microbial organism itself as a starting microbial organism, or transfer the appropriate enzyme-encoding portion of the genome(s) of such microbial organism(s) into the genome of the organism that has been already identified as being useful for large scale fermentation production. An example of this would be to select a microbial organism that already produces a suitable native thiamin dependent decarboxylase (DC) and native alcohol dehydrogenase (ADH), and use that microbial organism either as a starting organism or as a transformant organism to prepare a genetically modified microbial organism to produce a C6-C10 alcohol at higher yields or specificity than wild type microbial organisms.

EXAMPLE 1

Preparing the Modified LeuA (i.e., "LeuA'") Enzyme.

This example represents an embodiment wherein an engineered LeuA' enzyme is prepared. Such is accomplished beginning with an *Escherichia coli* organism that has been transformed with a plasmid containing a modified LeuA gene to produce a 2-isopropylmalate synthase variant (LeuA') having a higher-than-average catalytic efficiency ($k_{cat}/K_M$) for capturing 2-ketoacids of interest for catalysis. For this a particular gene that has been identified as being suitable is LeuA; GenBank Accession No. NC_000913.3 Gene ID: 947465.

In the expression $k_{cat}/K_M$, $k_{cat}$ is the "turnover number," of unit=$sec^{-1}$; $K_M$ is the Michaelis-Menten constant; and the turnover number equals $V_{Max}/[E]$, wherein $V_{Max}$ is maximum velocity, and [E] is the enzyme concentration. The equation applies to reactions obeying Michaelis-Menten kinetics, and generally provides the amount of substrate, in moles, that is converted to product in one second. The value $k_{cat}/K_M$ therefore indicates an effective catalysis capability and is obtained experimentally. The variants having a relatively higher $k_{cat}/K_M$ are therefore those that are more efficient at condensing 2-ketoacids (n=1-5 in intermediate I in FIG. 1), which may (in this exemplary FIG. 1) include 2-ketobutyrate, 2-ketovalerate, 2-ketocaproate, 2-ketoheptanoate, and/or 2-ketooctanoate, with acetyl CoA, thereby generating the corresponding 2-alkylmalate products (intermediate II in FIG. 1).

To prepare LeuA' variants substitutions are made at amino acid residue sites designated as Phe-47, Leu-73, His-97, Phe-99, Ser-139, and Asn-167. One or more of these targeted amino acids is/are converted to the amino acids glycine, alanine, leucine or valine by performing site-directed mutagenesis of the known LeuA gene of a selected organism, such as *E. coli* (GenBank: Accession No. NC_000913.3 Gene ID: 947465). See, also, U.S. Pat. No. 8,298,798 B2. A histidine "tag" (histidine-tag) may be attached to any given protein as an aid in purification of the protein. Following this "tagging," which may comprise a varying length sequence inserted at either end of a selected sequence and may include six (6) histidines and selected additional amino acids, the histidine-tagged enzyme, which constitutes a variant of the enzyme (i.e., a modified enzyme) (Leu A') which is expressed in the *E. coli* DE3 cells, is purified via nickel-nitrilotriacetic acid (Ni-NTA) chromatography. The efficiency of the purified variant enzyme in condensing the various 2-ketoacids (n=1-5 in intermediate I in FIG. 1) is determined by in vitro enzyme assays. For more information on one assay that may be suitable for this determination, see, e.g., Marcheschi, R. J.; Li, H.; Zhang, K.; Noey, E. L.; Kim, S.; Chaubey, A.; Houk, K. N.; Liao, J. C. "Synthetic recursive "+1" pathway for carbon chain elongation," *ACS Chem. Biol.*, 2012, 7:689-697. Variants displaying higher levels of catalytic efficiency ($k_{cat}/K_M$) are identified and selected for production of one or more desired C6-C10 alcohol(s). Combinations of variants of LeuA' that work together to catalyze the condensation of any or all of the identified 2-ketoacids involved in the C6-C10 alcohol biosynthesis may also be identified on the basis of in vitro assays.

FIG. 2 shows two routes to form 2-ketobutyrate from a carbon-containing substrate. The first is via a combination of a Wood-Ljungdahl syngas fixation pathway to form pyruvate, followed by a pyruvate to 2-ketobutyrate pathway, and the second is via a combination of a glycolysis or pentose phosphate pathway to form pyruvate, followed by a pyruvate to 2-ketobutyrate pathway. In either case, once 2-ketobutyrate is formed, the LeuABCD pathway begins chain elongation to produce the desired C7-C11 2-ketoacid (in this embodiment, 2-ketononanoate), and this C7-C11 2-ketoacid is then decarboxylated via a (thiamin dependent) decarboxylase to form the C6-C10 aldehyde having one less carbon than the C7-C11 2-ketoacid being decarboxylated (in this embodiment, octanal). Finally, the C6-C10 aldehyde is acted upon by an alcohol dehydrogenase to produce the corresponding C6-C10 alcohol (in this embodiment, 1-octanol).

EXAMPLE 2

I. Preparing *E. coli* LeuB' (Isopropylmalate Dehydrogenase) Variants Having Increased Activity Against 3-hexylmalate (3-HM).

During 2-ketononanoate biosynthesis by the recursive activity of the LeuABCD pathway, 3-alkylmalic acids of varying lengths are formed as substrates of LeuB. For efficient biosynthesis of 2-ketononanoate, it is desired that LeuB efficiently capture 3-ethylmalate (intermediate III, n=2; FIG. 1), 3-propylmalate (Intermediate III, n=3; FIG. 1), 3-butylmalate (3-BM; Intermediate III, n=4; FIG. 1), 3-pentylmalate (Intermediate III, n=5; FIG. 1) and 3-hexylmalate (3-HM; Intermediate III, n=6; FIG. 1) for catalysis. The native LeuB is relatively inefficient in capturing longer nonnatural 3-alkylmalate substrates. To improve the efficiency of native LeuB in capturing 3-hexylmalate for catalysis, the active site of native LeuB is modified using protein engineering techniques as described hereinbelow.

Residues lining the 3-isopropylmalate binding site of *E. coli* LeuB were identified from a structural model of LeuB that is constructed via homology modeling and using as the template the crystal structure model of *Thiobacillus ferrooxidans* isopropylmalate dehydrogenase (Protein Data Bank (PDB) code 1A05), as reported by Imada, K.; Inagaki, K.; Matsunami, H.; Kawaguchi, H.; Tanaka, H.; Tanaka, N.; Namba, K. "Structure of 3-isopropylmalate dehydrogenase in complex with 3-isopropylmalate at 2.0 Å resolution: the role of Glu88 in the unique substrate-recognition mechanism," *Structure*, 1998, 6:971-982. Leu-96 and Val-198 are selected for modification and variants are prepared wherein one or both is/are replaced, variously, with valine, alanine, and/or glycine, as shown in Table 1.

TABLE 1

| Enzyme* | Nucleotide sequence in the LeuB gene at indicated positions | |
|---|---|---|
| Wild type LeuB | 95-Leu-<u>Leu</u>-Pro-97<br>283-CTG<u>CTG</u>CCT-291 | 197-Asn-<u>Val</u>-Leu-199<br>589-AAC<u>GTG</u>CTG-597 |
| L96A | 283-CTG<u>GCC</u>CCT-291 | 589-AAC<u>GTG</u>CTG-597 |
| L96V | 283-CTG<u>GTG</u>CCT-291 | 589-AAC<u>GTG</u>CTG-597 |
| L96G | 283-CTG<u>GGT</u>CCT-291 | 589-AAC<u>GTG</u>CTG-597 |
| V198A | 283-CTG<u>CTG</u>CCT-291 | 589-AAC<u>GCG</u>CTG-597 |
| V198G | 283-CTG<u>CTG</u>CCT-291 | 589-AAC<u>GGT</u>CTG-597 |

TABLE 1-continued

| Enzyme* | Nucleotide sequence in the LeuB gene at indicated positions | |
|---|---|---|
| L96A/V198A | 283-CTG<u>GCC</u>CCT-291 | 589-AAC<u>GCC</u>CTG-597 |
| L96G/V198A | 283-CTG<u>GGT</u>CCT-291 | 589-AAC<u>GCG</u>CTG-597 |
| L96G/V198G | 283-CTG<u>GGT</u>CCT-291 | 589-AAC<u>GGT</u>CTG-597 |
| L96V/V198G | 283-CTG<u>GTG</u>CCT-291 | 589-AAC<u>GGT</u>CTG-597 |

*Enzymes are identified by the modifications made to the wild type amino acid sequence. The name of each includes a first letter which is the abbreviation for the wild type enzyme's amino acid; the number is its position within the amino acid sequence; and the last letter, which is the abbreviation for the amino acid substituted at that location. L = leucine; A = alanine; G = glycine; and V = valine.

For example, enzyme L96A is prepared by replacing Leu-96 in *E. coli* isopropylmalate dehydrogenase with alanine; enzyme L96G is prepared by replacing Leu-96 with glycine; and enzyme L96G/V198A is prepared by replacing Leu-96 with glycine and Val-198 with alanine. The remaining LeuB variants in the Table 1 are named according to the amino acid replaced.

Each of the engineered LeuB variants is expressed, purified, and then evaluated for activity against three substrates, which are 3-isopropylmalate (3-IPM), 3-butylmalate (3-BM), and 3-hexylmalate (3-HM). 3-IPM is the natural substrate of LeuB and is formed in the microbial organisms during the biosynthesis of leucine. The 3-BM and 3-HM are non-natural substrates of LeuB that would be formed inside the cells during C7-C11 2-ketoacid, for example, 2-ketononanoate, biosynthesis.

The evaluation of the LeuB variants is performed in two steps using the high-throughput enzyme assay described below. Initially, all the variants are tested for activity against a single high concentration of 3-IPM, 3-BM and 3-HM. Following the initial evaluation, detailed kinetic analysis is performed on a select number of variants to determine the maximal rate ($k_{cat}$), Michaelis-Menten constant ($K_M$), and the catalytic efficiency of the enzyme ($k_{cat}/K_M$).

LeuB' variants that are more efficient (higher $k_{cat}/K_M$) than the wild type enzyme in converting all or some of the 3-alkylmalate substrates, such as 3-HM, to the corresponding C7-C11 2-ketoacid, are desirable because they improve the overall efficiency of the relevant "+1" pathway.

II. Heterologous Expression of LeuB (Isopropylmalate Dehydrogenase) and its Engineered Variants in *E. coli*.

To evaluate the substrate specificity of the wild type LeuB and the engineered LeuB' variants listed in Table 1, genes of all the proteins are expressed into *E. coli* cells separately and the protein products isolated from the cells. To obtain the protein products, the LeuB gene sequence (EcoGene Accession No. EG11577 (Sequence Listing, SEQ ID 1) is downloaded from the EcoGene website (http://ecogene.org). Codons of an additional 11 amino acids are added after the codon of the last amino acid in the open reading frame of the LeuB gene. These additional amino acids include 6 histidines plus 5 additional amino acids, and are attached as a histidine-tag, to aid in purifying the protein in a single step using Ni-NTA chromatography. The gene sequence of the entire LeuB sequence with the 11 additional amino acids is chemically synthesized, cloned into the pETDuet-1 vector (EMD Biosciences), downstream of the T7 polymerase promoter, and sequenced by Synthetic Genomics Inc. (San Diego, Calif.). It is noted that none of the Sequence Listings included herein show the histidine-tag that is used, which in this case is Gly-Ser-Ser-His-His-His-His-His-His-Ser-Ser.

Genes of the LeuB' variants listed in Table 1 are also chemically synthesized following replacement of the codon of the selected amino acid (Leu-96 and/or V-198) with that of alanine, valine and/or glycine (Sequence Listing, SEQ ID 2 through SEQ ID 10) and cloned into the pETDuet-1 vector. The pETDuet-1 vector containing the LeuB or its variant gene is transformed into E. coli, and the LeuB or its variant is expressed and eventually purified as described below.

A. Transformation of E. coli:

E. coli expression studies are conducted using the competent BL21 (DE3) cells acquired from EMD Biosciences. Transformations are performed as per the kit instructions and involve mixing a 50 microliter (μL) aliquot of competent cells with 1 μL of the vector. Cells harboring the LeuB expression vector are selected using ampicillin as the marker.

B. Expression of LeuB and its Variants in E. coli:

E. coli transformants harboring the expression vector of LeuB or its variant are selected on LB agar plates containing 100 micrograms per milliliter (μg/mL) of ampicillin. The plates are incubated at 37 degrees Celsius (° C.) for 16 hours (h). A starter culture is started with transferring a single colony of transformant into 50 milliliters (mL) of Lysogeny Broth (LB) medium containing 100 μg/mL of ampicillin and incubated at 37° C. with shaking at 220 revolutions per minute (rpm) for overnight. Next day, 7 mL of starter culture is inoculated into 800 mL of Terrific Broth (TB) and the culture is incubated at 37° C. until the culture reaches an optical density at 600 nanometers (nm) ($OD_{600\ nm}$) of 0.5. Isopropyl β-D-1-thiogalactopyranoside (IPTG) at a final concentration of 1 millimolar (mM) is added to induce the expression of the LeuB or LeuB variant (LeuB') genes, and the culture is transferred to a 15° C. incubator for 16 h. At the end of 16 h, the culture is centrifuged at 8000 rpm to pelletize the cells. The cell pellet is divided into two aliquots and stored at −80° C. overnight before purification.

C. Purification of LeuB and its Variants:

An E. coli cell pellet from 400 mL of expression culture is suspended in B-PER reagent (Thermo Fisher Scientific, Inc., Rockford, Ill.) containing 1 μg/mL of DNAse (Thermo Fisher Scientific, Inc., Rockford, Ill.), 1 μg/mL of lysozyme (Thermo Fisher Scientific, Inc., Rockford, Ill.), 1 mM dithiothreitol (DTT), and protease inhibitor cocktail (RPI Corp., Mount Prospect, Ill.). The suspension is rocked gently for 30 minutes (min) at room temperature and centrifuged at 15,000 times gravity (×g) for 20 min to pelletize the cell debris. The supernatant is separated and incubated with 5 mL of Co-NTA resin (Thermo Fisher Scientific, Inc., Rockford, Ill.) that has been pre-equilibrated with an equilibration buffer (50 mM sodium phosphate, pH 8.0, containing 300 mM sodium chloride, 20 mM imidazole, 50 μL protease inhibitor cocktail, and 15 percent by volume (vol %) glycerol). Following an incubation period of 1 h at 4° C., the LeuB bound resin is washed with 5 volumes of equilibration buffer. LeuB and its variants are then eluted from the Co-NTA resin with an equilibration buffer containing 200 mM imidazole. The eluted proteins are finally dialyzed against phosphate buffered saline and stored as a 20 vol % glycerol solution at −20° C.

III. Determination of the Substrate Specificity of the Wild Type and the Engineered LeuB Variants.

The evaluation of the LeuB variants is performed in two steps using the high-throughput enzyme assay described below. Initially, all of the variants are screened for activity against a single high concentration of 3-IPM, 3-BM and 3-HM. Following the initial evaluation, detailed kinetic analysis is performed on a select number of variants to determine the maximal rate ($k_{cat}$), Michaelis-Menten constant ($K_M$), and the catalytic efficiency of the variant enzymes ($k_{cat}/K_M$).

A suitable spectrophotometric LeuB enzyme assay is adapted into a high-throughput format in 96-well plates for the kinetic evaluation of LeuB and its variants (shown in Table 1) against 3-isopropylmalate (3-IPM), 3-butylmalate (3-BM), and 3-hexylmalate (3-HM). See, for example, Hsu, Y.; Kohlhaw, G. B. "Leucine biosynthesis in Saccharomyces cerevisiae. Purification and characterization of beta-isopropylmalate dehydrogenase," J. Biol. Chem., 1980, 255:7255-7260. Steady state kinetic parameters ($k_{cat}$, $K_M$ and $k_{cat}/K_M$) for the oxidative decarboxylation of the three substrates by the variants are determined in these experiments.

A. HTP Screening Assay for the Identification of Functional LeuB Variants:

The HTP screening assay involves incubating 750 micromoles (μM) of 3-IPM, 1 mM 3-BM or 1 mM 3-HM, with 2 mM nicotinamide adenine dinucleotide ($NAD^+$) in LeuB assay buffer (50 mM 4-(2-hydroxyethyl) piperazine-1-ethanesulfonic acid (HEPES), pH 8.0, containing 30 mM potassium chloride (KCl) and 5 mM magnesium chloride ($MgCl_2$)) at 25° C. The reaction is started by the addition at 25° C. of working enzyme stock containing from 0.3 microgram (μg) to 1.1 μg of LeuB variant diluted in assay buffer containing 1 mM DTT and 1 milligram per milliliter (mg/mL) bovine serum albumin (BSA). The plate containing the 200 μL of reaction mixture is centrifuged at 2500×g for 15 seconds (sec) and the absorbance change of the reaction mixture is followed spectrophotometrically at 340 nm on a BioTek™ plate reader, pre-equilibrated at 25° C. Initial velocity of the enzyme reaction is calculated from the rate of NADH production at 340 nm and using the extinction coefficient of NADH (6.22 per millimolar per centimeter ($mM^{-1}cm^{-1}$)). The activity of all the variants is normalized with the amount of enzyme present in the reaction mixture and expressed as nanomoles per minute per microgram ($nmol \cdot min^{-1} \cdot \mu g^{-1}$) (Table 2). Protein concentrations for normalizing the activities are determined using the 660 nm total protein assay kit acquired from Pierce Biotechnology Inc.™, available from Thermo Fisher Scientific, Inc., and using BSA as the standard.

B. HTP LeuB Enzyme Assay for the Determination of the Kinetic Parameters of Oxidative Decarboxylation of 3-IPM, 3-BM and 3-HM by LeuB Variants:

The HTP kinetic assay involves incubating eight varied concentrations, of 3-IPM (from 0 to 1.2 mM) or 3-BM (from 0 to 2 mM) or 3-HM (from 0 to 2 mM), with 2 mM $NAD^+$ in LeuB assay buffer (50 mM HEPES, pH 8.0, containing 30 mM KCl and 5 mM $MgCl_2$) at 25° C. The reaction is started by adding from 0.008 μg to 0.5 μg of LeuB variant which has been pre-diluted in assay buffer containing 1 mM DTT and 1 mg/mL BSA. The plate containing the 200 μl of reaction mixture is centrifuged at 2500×g for 15 sec and the absorbance change is followed spectrophotometrically at 340 nm on a BioTek™ plate reader maintained at 25° C. Initial velocity of the enzyme reaction is calculated from the rate of NADH production at 340 nm and using the extinction coefficient of NADH (6.22 $mM^{-1}cm^{-1}$). The kinetic parameters ($k_{cat}$, $K_M$ and $k_{cat}/K_M$) of oxidative decarboxylation of 3-alkylmalate are determined by fitting the data to the Michaelis-Menten equation using nonlinear regression performed using the GraphPad Prism™ software. Table 3 lists the kinetic parameters of the wild type and engineered variants against the three substrates. The amount of enzyme in the reaction mixture is determined using the 660 nm total protein assay kit acquired from Pierce Biotechnology Inc.™, using BSA as the standard.

C. Results and Discussion

To improve the efficiency of the "+1" pathway in producing 2-ketononanoate, the isopropylmalate dehydrogenase would desirably efficiently catalyze the oxidative decarboxylation of all of the intermediate 3-alkylmalates. The three substrates used for the evaluation of LeuB variants are representative of these intermediate 3-alkylmalates, i.e., 3-isopropylmalate (3-IPM) is representative of the shorter 3-alkylmalate substrates expected to form during the earlier cycles of the "+1" iterative pathway; 3-butylmalate (3-BM) is representative of the intermediate-length 3-alkylmalates; and formation; and 3-hexylmalate (3-HM) would be oxidatively decarboxylated by LeuB to form 2-ketono-nanoate.

Initially the LeuB' variants are screened for activity against a single high concentration of each of 3-IPM, 3-BM and 3-HM (Table 2).

TABLE 2

Evaluation of the Wild type LeuB and LeuB' variants.

| Enzyme | *Specific activity, nmol · min$^{-1}$ · ug$^{-1}$ | | |
|---|---|---|---|
| | 3-IPM | 3-BM | 3-HM |
| Wild type LeuB | 18.3 | 4.3 | 0.68 |
| L96A | 15.4 | 9.48 | 0.77 |
| L96V | 1.53 | ND | ND |
| L96G | 2.90 | 1.5 | 9.5 |
| V198A | 2.83 | 1.81 | 2.5 |
| V198G | 4.66 | 1.83 | 0.5 |
| L96A/V198A | 0.65 | 1.26 | 3.3 |
| L96G/V198A | ND | 1.49 | 20.4 |
| L96G/V198G | 0.02 | 0.08 | 3.6 |
| L96V/V198G | 0.05 | 0.04 | ND |

*The specific activity of LeuB variants against the three substrates, 3-isopropylmalate (3-IPM), 3-butylmalate (3-BM), and 3-hexylmalate (3-HM) is determined as described in the HTP screening assay. The specific activities shown are the means of duplicated experiments from the screening assay. The range between the two values is less than 20%. ND = not detected under experimental conditions.

Without wishing to be bound by any theory, the results illustrated in Table 2 may be interpreted as suggesting that replacing Leu-96 and/or Val-198 with amino acids having smaller hydrophobic side chains, e.g., valine, alanine, or glycine, may in some instances simultaneously decrease enzyme activity against 3-IPM, and increase enzyme activity against 3-HM.

Variants L96A, L96G, V198A, L96A/V198A, L96G/V198A, and L96G/V198G exhibit higher activity than the wild type enzyme against 3-HMe and are subjected to further kinetic analysis. This analysis suggests that the wild type LeuB is highly efficient in capturing its native substrate, 3-IPM for catalysis. As illustrated in Table 3, the catalytic efficiency of the wild type enzyme is found to be 1,000-fold higher than that of the 3-HM, and the efficiency of capturing 3-BM is intermediate of the two substrates. The wild type LeuB enzyme thus becomes a progressively poorer catalyst as the "+1" pathway iterates for elongating 2-ketobutyrate to a C7-C11 2-ketoacid, such as, in this instance, 2-ketononanoate.

Substituting Leu-96 in the *E. coli* LeuB with progressively smaller residues, e.g., alanine (L96A) or glycine (L96G), results in improving the efficiency of capturing substrates with longer alkyl chains, with a concomitant reduction in capturing substrates with shorter alkyl chains. The L96A variant is approximately 4-fold more inefficient at capturing 3-IPM than the wild type enzyme, while being modestly poor in capturing 3-BM (see Table 3). The L96G variant is 100-fold less efficient than the wild type enzyme in capturing 3-IPM, while being 80-fold more efficient at capturing 3-HM than the wild type enzyme. This suggests that Leu-96 is blocking the capture of longer alkylmalates, such as 3-HM.

Substituting Val-198 in the *E. coli* LeuB with a smaller amino acid residue, e.g., alanine, improves the catalytic efficiency of the enzyme in capturing longer 3-alkylmalates, such as 3-HM, while decreasing the efficiency of capturing shorter alkylmalates, such as 3-IPM. This is evident from the comparative efficiencies of the V198A variant in catalyzing the conversion of 3-HM, which is 5-fold higher, and of 3-IPM, which is 1,000-fold lower, when compared to the efficiencies of the wild type LeuB (see Table 3).

TABLE 3

Substrate specificity of engineered LeuB enzymes

| Enzyme | Substrate | $k_{cat}$ min$^{-1}$ | $K_M$ mM | $K_{cat}/K_M$, Min$^{-1}$ · mM$^{-1}$ |
|---|---|---|---|---|
| Wild typeLeuB | 3-IPM | 1435 ± 121 | 0.009 ± .003 | 167,805 ± 39,622 |
| | 3-BM | 219 ± 20 | 0.038 ± 0.013 | 6274 ± 1778 |
| | 3-HM | 26 ± 2 | 0.16 ± 0.02 | 166 ± 16 |
| L96A | 3-IPM | 666 ± 154 | 0.016 ± 0.01 | 45,447 ± 13,020 |
| | 3-BM | 420 ± 22 | 0.13 ± 0.02 | 3315 ± 372 |
| | 3-HM | 41 ± 0.5 | 0.24 ± 0.04 | 179 ± 33 |
| L96A/V198A | 3-IPM | * | * | 36 ± 12 |
| | 3-BM | * | * | 67 ± 6 |
| | 3-HM | 159 ± 4 | 0.08 ± 0.01 | 2008 ± 287 |
| V198A | 3-IPM | * | * | 151 ± 71 |
| | 3-BM | * | * | 94 ± 26 |
| | 3-HM | 97 ± 33 | 0.11 ± 0.01 | 898 ± 333 |
| L96G | 3-IPM | * | * | 178 ± 41 |
| | 3-BM | 187 ± 6 | 1.9 ± 0.2 | 94 ± 6 |
| | 3-HM | 455 ± 10 | 0.03 ± 0.003 | 13,159 ± 754 |
| L96G/V198A | 3-IPM | * | * | 60 ± 9 |
| | 3-BM | 268 ± 21 | 3.3 ± 0.4 | 79 ± 3 |
| | 3-HM | 874 ± 23 | 0.05 ± 0.0005 | 16,932 ± 217 |

3-IPM = 3-isopropylmalate; 3-BM = 3-butylmalate; and 3-HM = 3-hexylmalate. For LeuB' variants having high Michaelis-Menten constant ($K_M$) against one of the substrates, only the catalytic efficiency ($k_{cat}/K_M$) is reported. Mean ± standard deviation (S.D.) from a minimum of three independent experiments is shown.
*Indicates that activity is low and, therefore, the parameter cannot be calculated.

It is also noted that substitution of both Leu-96 and Val-98 with smaller hydrophobic residues simultaneously increase in efficiency of capturing 3-HM and decreases the efficiency of capturing 3-IPM. The L96A/V198A and L96G/V198A variants exhibit a 12- and 102-fold greater efficiency, respectively, in capturing 3-HM compared with the wild type enzyme (Table 3), while at the same time these variants are very poor catalysts for 3-IPM, as evident from a drop of more than 3000-fold when compared with the wild type LeuB enzyme.

The data shows that the genetically modified LeuB' enzyme is generally operates at a higher catalytic efficiency than that of the wild type enzyme to catalyze, as shown, 3-butylmalate to form 2-ketoheptanoate, or 3-hexylmalate to form 2-ketononanoate. It can also be inferred that it will more efficiency catalyze 3-pentylmalate to form 2-ketooctanoate. Finally, it will also carry out combinations of these conversions at a higher catalytic efficiency.

Kinetic data on LeuB' variants suggests that one means of efficient formation of a C7-C11 2-ketoacid, such as but not limited to 2-ketononanoate, by the iteration of the "+1" pathway would be realized by coexpression of the wild type LeuB enzyme and one or more of the variants listed in Table 3.

EXAMPLE 3

Preparing the Modified LeuCD (i.e., "LeuCD'") Enzymes.

In this Example 3 embodiment an approach similar to that used for the LeuA' enzyme in Example 1 is described. The process begins with an *E. coli* organism that has been transformed with a plasmid containing the LeuC and LeuD genes so that it produces a modified 2-isopropylmalate isomerase complex with higher catalytic efficiency ($k_{cat}/K_M$) at isomerizing 2-alkylmalates (n=1-5 in Intermediate II, FIG. 1) generated by LeuA' to their corresponding 3-alkylmalates (n=1-5 in Intermediate III, FIG. 1). The modified LeuC and LeuD genes are made synthetically by altering some of the genetic codes, i.e., substituting one or more of the amino acids in the amino acid sequence, of LeuC and LeuD genes obtained from GenBank (LeuC: GenBank Accession No. NC 000913.3 Gene ID: 945076; and LeuD: GenBank Accession No. NC 000913.3, Gene ID: 945642). Each engineered variant is made by replacing one or more residues within and/or near the active sites of LeuC and/or LeuD using site-directed mutagenesis. Each modified enzyme is expressed as a histidine-tagged protein in *E. coli* DE3 cells and then purified using Ni-NTA chromatography. The efficiency of the purified variant enzyme in isomerizing various 2-alkylmalates is determined by an in vitro coupled enzyme assay such as may be used to assay for aconitase. See, e.g., Han, D.; Canali, R.; Garcia, J.; Aguilera, R.; Gallaher, T. K.; Cadenas, E. "Sites and mechanisms of aconitase inactivation by peroxynitrite: Modulation by citrate and glutathione," *Biochemistry*, 2005, 44:11986-11996. Variants displaying higher catalytic efficiency ($k_{CAT}/K_M$) than the native enzyme complex are identified and selected for production of a C6-C10 alcohol, such as 1-octanol. Combinations of variants of LeuCD' that work together to catalyze the isomerization of all the intermediate 2-alkylmalates (n=1-5 in intermediate II, FIG. 1) involved in biosynthesis of an applicable C7-C11 2-ketoacid, such as 2-ketononanoate, are also identified on the basis of in vitro assays.

EXAMPLE 4

Preparing the Modified DC ("DC'", Thiamin Dependent Decarboxylase) Enzyme.

In this Example 4 embodiment a process similar to that used for the LeuA' enzyme, as described in Example 1, is employed. The process begins with an engineered ketoisovalerate decarboxylase (for example, from *Lactococcus lactis* subsp. *lactis* strain IFPL730, GenBank Accession No. AJ746364.1 GI:51870501) or thiamin diphosphate dependent phenylpyruvate decarboxylase (for example, from *Saccharomycs cerevisiae* (gene YDR380W) or *Azospirillum brasilense* (GeneBank Accession No. L26240.1). Each engineered variant is made by replacing one or more amino acids within and/or near the active sites by conversion of the original amino acid to glycine, alanine, leucine or valine using site-directed mutagenesis. Variants displaying relatively lower catalytic efficiency ($k_{CAT}/K_M$) for smaller 2-ketoacids (n=1-5 in intermediate I, FIG. 1) but which retain or show relatively higher efficiency for a C7-C11 2-ketoacid, such as 2-ketononanoate, are identified and selected for production of a desired C6-C10 alcohol, such as 1-octanol. (It is noted that, in the case of phenylpyruvate decarboxylases, the engineered enzymes may be generally poorer than the wild type enzyme in catalyzing the conversion of phenylpyruvic acid. Each modified enzyme is expressed as a histidine-tagged protein, expressed heterologously in *E. coli* DE3 cells, and purified using Ni-NTA chromatography. The efficiency of the purified variant enzyme, in decarboxylating a desired C7-C11 2-ketoacids, such as 2-ketononanoate, to form a C6-C10 aldehyde having one less carbon atom than the C7-C11 2-ketoacid being converted, for example, octanal, is determined by in vitro coupled enzyme assays. One suitable assay method that may be used for this purpose is described in, e.g., Zhang, K.; Sawaya, M. R.; Eisenberg, D. S.; Liao, J. C. "Expanding metabolism for biosynthesis of nonnatural alcohols," *Proc. Natl. Acad. Sci. USA*, 2008, 105:20653-20658.

EXAMPLE 5

Preparing the Modified ADH ("ADH'", Alcohol Dehydrogenase) Enzyme.

This preparation may be accomplished in a manner similar to that used for the LeuA' enzyme, as described in Example 1. In this case the process begins with an engineered human (GenBank Accession No. NP_000662.3 GI:71565154) or *E. coli* (GenBank Accession No. NC_000913.3 Gene ID: 944988) Class III alcohol dehydrogenase, that is capable of reducing a C6-C10 aldehyde, such as octanal, to a corresponding C6-C10 alcohol, such as 1-octanol. In certain embodiments the starting alcohol dehydrogenase may be an ADH from *Saccharomyces cerevisiae*. Each engineered variant may then be made by replacing one or more amino acid residues within and/or near the active sites of the selected alcohol dehydrogenase, e.g., a Class III alcohol dehydrogenase, using site-directed mutagenesis. Engineered enzymes will have higher catalytic efficiency ($k_{cat}/K_M$) than the native enzyme in reducing the selected C6-C10 aldehyde, such as octanal, to the corresponding C6-C10 alcohol, such as 1-octanol. Each modified enzyme is then expressed as a histidine-tagged protein, expressed heterologously in *E. coli* DE3 cells, and purified using Ni-NTA chromatography. The efficiency of the purified variant enzyme in reducing the C6-C10 aldehyde is determined by in vitro enzyme assay. A suitable assay method is described in, e.g., Sanghani, P. C.; Stone, C. L.; Ray, B. D.; Pindel, E. V.; Hurley, T. D.; Bosron, W. F. "Kinetic mechanism of human glutathione-dependent formaldehyde dehydrogenase," *Biochemistry*, 2000, 39:10720-10729. Variants displaying higher catalytic efficiency ($k_{cat}/K_M$) for the C6-C10 aldehyde are identified and selected for C6-C10 alcohol production.

The invention claimed is:

1. A process for preparing $C_7$-$C_{11}$ 2-ketoacid, the process comprising:
   (I) providing at least one of a $C_4$-$C_{10}$ 2-ketoacid substrate with:
   (1) a LeuA enzyme having isopropylmalate synthase activity;
   (2) a genetically modified LeuB' enzyme, the genetically modified LeuB' enzyme comprising the amino acid sequence of SEQ ID NO: 2 and comprising at least one mutation wherein alanine or glycine is independently substituted for Leu-96, Val-198, or a combination thereof; and
   (3) a LeuCD' enzyme complex having isopropylmalate isomerase activity;
   under conditions that the at least one of the $C_4$-$C_{10}$ 2-ketoacid substrate is converted to the $C_7$-$C_{11}$ 2-ketoacid; wherein the at least one genetically modified LeuB' enzyme complex has isopropylmalate dehydrogenase activity; and wherein the conversion of the at least one of the $C_4$-$C_{10}$ 2-ketoacid substrate to the $C_7$-$C_{11}$ 2-ketoacid occurs via one or more biochemical reactions.

2. The process of claim 1, wherein the amino acid sequence of the Leu B' enzyme comprises a mutation selected from the group consisting of:
   (1) glycine for Leu-96;
   (2) alanine for Val-198;
   (3) alanine for Leu-96 and alanine for Val-198;
   (4) glycine for Leu-96 and alanine for Val-198;
   (5) glycine for Leu-96 and glycine for Val-198; and
   (6) alanine for Leu-96.

3. The process of claim 1, wherein the at least one of the $C_4$-$C_{10}$ 2-ketoacid substrate comprises 2-ketobutyrate.

4. The process of claim 1, wherein the at least one of the $C_4$-$C_{10}$ 2-ketoacid substrate comprises 2-ketoisovalerate.

5. The process of claim 1, further comprising: (II) providing the $C_7$-$C_{11}$ 2-ketoacid with a thiamin dependent decarboxylase having thiamin dependent decarboxylase activity, under conditions that the $C_7$-$C_{11}$ 2-ketoacid is converted to a $C_6$-$C_{10}$ aldehyde having one less carbon atom than the $C_7$-$C_{11}$ 2-ketoacid being converted.

6. The process of claim 5, wherein (I) and (II) independently occur within or outside of a genetically modified microbial organism.

7. The process of claim 5, further comprising: (III) providing the $C_6$-$C_{10}$ aldehyde with an alcohol dehydrogenase having alcohol dehydrogenase activity, under conditions that the $C_6$-$C_{10}$ aldehyde is converted to a corresponding $C_6$-$C_{10}$ alcohol.

8. The process of claim 5, further comprising: (III) providing the $C_6$-$C_{10}$ aldehyde with an aldehyde dehydrogenase having aldehyde dehydrogenase activity, under conditions that the $C_6$-$C_{10}$ aldehyde is converted to a corresponding $C_6$-$C_{10}$ carboxylic acid.

9. The process of claim 5, further comprising: (III) providing the $C_6$-$C_{10}$ aldehyde with an aldehyde decarbonylase having fatty aldehyde decarbonylase activity, under conditions that the $C_6$-$C_{10}$ aldehyde is converted to a corresponding $C_{n-1}$ alkane.

10. The process of claim 1, further comprising providing (4) a native LeuB enzyme.

11. A microbial organism comprising:
    a genetically modified LeuB' enzyme comprising the amino acid sequence of SEQ ID NO: 2 and comprising at least one modification wherein alanine or glycine is independently substituted for Leu-96, Val-198, or a combination thereof and having isopropylmalate dehydrogenase activity.

12. The microbial organism of claim 11, wherein the amino acid sequence of the LeuB' enzyme comprises a mutation selected from the group consisting of:
    (1) glycine for Leu-96;
    (2) alanine for Val-198;
    (3) alanine for Leu-96 and alanine for Val-198;
    (4) glycine for Leu-96 and alanine for Val-198;
    (5) glycine for Leu-96 and glycine for Val-198;
    and (6) alanine for Leu-96.

13. A genetically modified LeuB' polypeptide having isopropylmalate dehydrogenase activity, the polypeptide comprising the amino acid sequence of SEQ ID NO: 2 and comprising at least one mutation wherein alanine or glycine is independently substituted for Leu-96, Val-198, or a combination thereof.

14. The genetically modified LeuB'polypeptide of claim 13, wherein the amino acid sequence of the LeuB' enzyme comprises a mutation selected from the group consisting of:
    (1) glycine for Leu-96;
    (2) alanine for Val-198;
    (3) alanine for Leu-96 and alanine for Val-198;
    (4) glycine for Leu-96 and alanine for Val-198;
    (5) glycine for Leu-96 and glycine for Val-198;
    and (6) alanine for Leu-96.

* * * * *

SEQUENCE LISTING

<160> NUMBER OF SEQ ID NOS: 20

<210> SEQ ID NO 1
<211> LENGTH: 1089
<212> TYPE: DNA
<213> ORGANISM: Escherichia coli
<220> FEATURE:
<221> NAME/KEY: CDS
<222> LOCATION: (1)..(1089)
<220> FEATURE:
<221> NAME/KEY: gene
<222> LOCATION: (1)..(1089)
<223> OTHER INFORMATION: Wild type E.coli LeuB
<220> FEATURE:
<221> NAME/KEY: mat_peptide
<222> LOCATION: (1)..(1089)

<400> SEQUENCE: 1

| | | | | | | | | | | | | | | | | |
|---|---|---|---|---|---|---|---|---|---|---|---|---|---|---|---|---|
| atg | tcg | aag | aat | tac | cat | att | gcc | gta | ttg | ccg | ggg | gac | ggt | att | ggt | 48 |
| Met | Ser | Lys | Asn | Tyr | His | Ile | Ala | Val | Leu | Pro | Gly | Asp | Gly | Ile | Gly | |
| 1 | | | | 5 | | | | 10 | | | | | 15 | | | |

| | | | | | | | | | | | | | | | | |
|---|---|---|---|---|---|---|---|---|---|---|---|---|---|---|---|---|
| ccg | gaa | gtg | atg | acc | cag | gcg | ctg | aaa | gtg | ctg | gat | gcc | gtg | cgc | aac | 96 |
| Pro | Glu | Val | Met | Thr | Gln | Ala | Leu | Lys | Val | Leu | Asp | Ala | Val | Arg | Asn | |
| | | | 20 | | | | | 25 | | | | | 30 | | | |

| | | | | | | | | | | | | | | | | |
|---|---|---|---|---|---|---|---|---|---|---|---|---|---|---|---|---|
| cgc | ttt | gcg | atg | cgc | atc | acc | acc | agc | cat | tac | gat | gta | ggc | ggc | gca | 144 |
| Arg | Phe | Ala | Met | Arg | Ile | Thr | Thr | Ser | His | Tyr | Asp | Val | Gly | Gly | Ala | |
| | | 35 | | | | | 40 | | | | | 45 | | | | |

| | | | | | | | | | | | | | | | | |
|---|---|---|---|---|---|---|---|---|---|---|---|---|---|---|---|---|
| gcc | att | gat | aac | cac | ggg | caa | cca | ctg | ccg | cct | gcg | acg | gtt | gaa | ggt | 192 |
| Ala | Ile | Asp | Asn | His | Gly | Gln | Pro | Leu | Pro | Pro | Ala | Thr | Val | Glu | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| tgt | gag | caa | gcc | gat | gcc | gtg | ctg | ttt | ggc | tcg | gta | ggc | ggc | ccg | aag | 240 |
| Cys | Glu | Gln | Ala | Asp | Ala | Val | Leu | Phe | Gly | Ser | Val | Gly | Gly | Pro | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tgg | gaa | cat | tta | cca | cca | gac | cag | caa | cca | gaa | cgc | ggc | gcg | ctg | ctg | 288 |
| Trp | Glu | His | Leu | Pro | Pro | Asp | Gln | Gln | Pro | Glu | Arg | Gly | Ala | Leu | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| cct | ctg | cgt | aag | cac | ttc | aaa | tta | ttc | agc | aac | ctg | cgc | ccg | gca | aaa | 336 |
| Pro | Leu | Arg | Lys | His | Phe | Lys | Leu | Phe | Ser | Asn | Leu | Arg | Pro | Ala | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| ctg | tat | cag | ggg | ctg | gaa | gca | ttc | tgt | ccg | ctg | cgt | gca | gac | att | gcc | 384 |
| Leu | Tyr | Gln | Gly | Leu | Glu | Ala | Phe | Cys | Pro | Leu | Arg | Ala | Asp | Ile | Ala | |
| | | | 115 | | | | | 120 | | | | | 125 | | | |

| | | | | | | | | | | | | | | | | |
|---|---|---|---|---|---|---|---|---|---|---|---|---|---|---|---|---|
| gca | aac | ggc | ttc | gac | atc | ctg | tgt | gtg | cgc | gaa | ctg | acc | ggc | ggc | atc | 432 |
| Ala | Asn | Gly | Phe | Asp | Ile | Leu | Cys | Val | Arg | Glu | Leu | Thr | Gly | Gly | Ile | |
| | | 130 | | | | | 135 | | | | | 140 | | | | |

| | | | | | | | | | | | | | | | | |
|---|---|---|---|---|---|---|---|---|---|---|---|---|---|---|---|---|
| tat | ttc | ggt | cag | cca | aaa | ggc | cgc | gaa | ggt | agc | gga | caa | tat | gaa | aaa | 480 |
| Tyr | Phe | Gly | Gln | Pro | Lys | Gly | Arg | Glu | Gly | Ser | Gly | Gln | Tyr | Glu | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gcc | ttt | gat | acc | gag | gtg | tat | cac | cgt | ttt | gag | atc | gaa | cgt | atc | gcc | 528 |
| Ala | Phe | Asp | Thr | Glu | Val | Tyr | His | Arg | Phe | Glu | Ile | Glu | Arg | Ile | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| cgc | atc | gcg | ttt | gaa | tct | gct | cgc | aag | cgt | cgc | cac | aaa | gtg | acg | tcg | 576 |
| Arg | Ile | Ala | Phe | Glu | Ser | Ala | Arg | Lys | Arg | Arg | His | Lys | Val | Thr | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| atc | gat | aaa | gcc | aac | gtg | ctg | caa | tcc | tct | att | tta | tgg | cgg | gag | atc | 624 |
| Ile | Asp | Lys | Ala | Asn | Val | Leu | Gln | Ser | Ser | Ile | Leu | Trp | Arg | Glu | Ile | |
| | | | 195 | | | | | 200 | | | | | 205 | | | |

| | | | | | | | | | | | | | | | | |
|---|---|---|---|---|---|---|---|---|---|---|---|---|---|---|---|---|
| gtt | aac | gag | atc | gcc | acg | gaa | tac | ccg | gat | gtc | gaa | ctg | gcg | cac | atg | 672 |
| Val | Asn | Glu | Ile | Ala | Thr | Glu | Tyr | Pro | Asp | Val | Glu | Leu | Ala | His | Met | |
| | | 210 | | | | | 215 | | | | | 220 | | | | |

| | | | | | | | | | | | | | | | | |
|---|---|---|---|---|---|---|---|---|---|---|---|---|---|---|---|---|
| tac | atc | gac | aac | gcc | acc | atg | cag | ctg | att | aaa | gat | cca | tca | cag | ttt | 720 |
| Tyr | Ile | Asp | Asn | Ala | Thr | Met | Gln | Leu | Ile | Lys | Asp | Pro | Ser | Gln | Phe | |
| 225 | | | | | 230 | | | | | 235 | | | | | 240 | |

```
gac gtt ctg ctg tgc tcc aac ctg ttt ggc gac att ctg tct gac gag     768
Asp Val Leu Leu Cys Ser Asn Leu Phe Gly Asp Ile Leu Ser Asp Glu
            245                 250                 255 tgc gca atg atc act ggc tcg atg ggg atg ttg cct tcc gcc agc ctg     816
Cys Ala Met Ile Thr Gly Ser Met Gly Met Leu Pro Ser Ala Ser Leu
        260                 265                 270 aac gag caa ggt ttt gga ctg tat gaa ccg gcg ggc tcg gca cca         864
Asn Glu Gln Gly Phe Gly Leu Tyr Glu Pro Ala Gly Ser Ala Pro
    275                 280                 285 gat atc gca ggc aaa aac atc gcc aac ccg att gca caa atc ctt tcg     912
Asp Ile Ala Gly Lys Asn Ile Ala Asn Pro Ile Ala Gln Ile Leu Ser
290                 295                 300 ctg gca ctg ctg ctg cgt tac agc ctg gat gcc gat gat gcg gct tgc     960
Leu Ala Leu Leu Leu Arg Tyr Ser Leu Asp Ala Asp Asp Ala Ala Cys
305                 310                 315                 320 gcc att gaa cgc gcc att aac cgc gca tta gaa gaa ggc att cgc acc    1008
Ala Ile Glu Arg Ala Ile Asn Arg Ala Leu Glu Glu Gly Ile Arg Thr
                325                 330                 335 ggg gat tta gcc cgt ggc gct gcc gcc gtt agt acc gat gaa atg ggc    1056
Gly Asp Leu Ala Arg Gly Ala Ala Ala Val Ser Thr Asp Glu Met Gly
            340                 345                 350 gat atc att gcc cgc tat gta gca gaa ggg gtg                        1089
Asp Ile Ile Ala Arg Tyr Val Ala Glu Gly Val
        355                 360

<210> SEQ ID NO 2
<211> LENGTH: 363
<212> TYPE: PRT
<213> ORGANISM: Escherichia coli

<400> SEQUENCE: 2

Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
            20                  25                  30

Arg Phe Ala Met Arg Ile Thr Thr Ser His Tyr Asp Val Gly Gly Ala
        35                  40                  45

Ala Ile Asp Asn His Gly Gln Pro Leu Pro Ala Thr Val Glu Gly
    50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Leu
                85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
        115                 120                 125

Ala Asn Gly Phe Asp Ile Leu Cys Val Arg Glu Leu Thr Gly Gly Ile
    130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg Arg His Lys Val Thr Ser
            180                 185                 190

Ile Asp Lys Ala Asn Val Leu Gln Ser Ser Ile Leu Trp Arg Glu Ile
        195                 200                 205
```

```
Val Asn Glu Ile Ala Thr Glu Tyr Pro Asp Val Glu Leu Ala His Met
    210                 215                 220
Tyr Ile Asp Asn Ala Thr Met Gln Leu Ile Lys Asp Pro Ser Gln Phe
225                 230                 235                 240
Asp Val Leu Leu Cys Ser Asn Leu Phe Gly Asp Ile Leu Ser Asp Glu
                245                 250                 255
Cys Ala Met Ile Thr Gly Ser Met Gly Met Leu Pro Ser Ala Ser Leu
            260                 265                 270
Asn Glu Gln Gly Phe Gly Leu Tyr Glu Pro Ala Gly Gly Ser Ala Pro
        275                 280                 285
Asp Ile Ala Gly Lys Asn Ile Ala Asn Pro Ile Ala Gln Ile Leu Ser
    290                 295                 300
Leu Ala Leu Leu Leu Arg Tyr Ser Leu Asp Ala Asp Ala Ala Cys
305                 310                 315                 320
Ala Ile Glu Arg Ala Ile Asn Arg Ala Leu Glu Glu Gly Ile Arg Thr
                325                 330                 335
Gly Asp Leu Ala Arg Gly Ala Ala Val Ser Thr Asp Glu Met Gly
            340                 345                 350
Asp Ile Ile Ala Arg Tyr Val Ala Glu Gly Val
        355                 360

<210> SEQ ID NO 3
<211> LENGTH: 1089
<212> TYPE: DNA
<213> ORGANISM: Artificial Sequence
<220> FEATURE:
<223> OTHER INFORMATION: Synthesized - SEQ ID NO:2 L96A
<220> FEATURE:
<221> NAME/KEY: mat_peptide
<222> LOCATION: (1)..(1089)
<220> FEATURE:
<221> NAME/KEY: gene
<222> LOCATION: (1)..(1089)
<223> OTHER INFORMATION: SEQ ID NO:2 L96A
<220> FEATURE:
<221> NAME/KEY: CDS
<222> LOCATION: (1)..(1089)

<400> SEQUENCE: 3 atg tcg aag aat tac cat att gcc gta ttg ccg ggg gac ggt att ggt    48
Met Ser Lys Asn Tyr His Ile Ala Val Leu Pro Gly Asp Gly Ile Gly
1               5                   10                  15 ccg gaa gtg atg acc cag gcg ctg aaa gtg ctg gat gcc gtg cgc aac    96
Pro Glu Val Met Thr Gln Ala Leu Lys Val Leu Asp Ala Val Arg Asn
                20                  25                  30 cgc ttt gcg atg cgc atc acc acc agc cat tac gat gta ggc ggc gca   144
Arg Phe Ala Met Arg Ile Thr Thr Ser His Tyr Asp Val Gly Gly Ala
            35                  40                  45 gcc att gat aac cac ggg caa cca ctg ccg cct gcg acg gtt gaa ggt   192
Ala Ile Asp Asn His Gly Gln Pro Leu Pro Pro Ala Thr Val Glu Gly
        50                  55                  60 tgt gag caa gcc gat gcc gtg ctg ttt ggc tcg gta ggc ggc ccg aag   240
Cys Glu Gln Ala Asp Ala Val Leu Phe Gly Ser Val Gly Gly Pro Lys
65                  70                  75                  80 tgg gaa cat tta cca cca gac cag caa cca gaa cgc ggc gcg ctg gcc   288
Trp Glu His Leu Pro Pro Asp Gln Gln Pro Glu Arg Gly Ala Leu Ala
                85                  90                  95 cct ctg cgt aag cac ttc aaa tta ttc agc aac ctg cgc ccg gca aaa   336
Pro Leu Arg Lys His Phe Lys Leu Phe Ser Asn Leu Arg Pro Ala Lys
                100                 105                 110
```

```
ctg tat cag ggg ctg gaa gca ttc tgt ccg ctg cgt gca gac att gcc    384
Leu Tyr Gln Gly Leu Glu Ala Phe Cys Pro Leu Arg Ala Asp Ile Ala
        115                 120                 125 gca aac ggc ttc gac atc ctg tgt gtg cgc gaa ctg acc ggc ggc atc    432
Ala Asn Gly Phe Asp Ile Leu Cys Val Arg Glu Leu Thr Gly Gly Ile
    130                 135                 140 tat ttc ggt cag cca aaa ggc cgc gaa ggt agc gga caa tat gaa aaa    480
Tyr Phe Gly Gln Pro Lys Gly Arg Glu Gly Ser Gly Gln Tyr Glu Lys
145                 150                 155                 160 gcc ttt gat acc gag gtg tat cac cgt ttt gag atc gaa cgt atc gcc    528
Ala Phe Asp Thr Glu Val Tyr His Arg Phe Glu Ile Glu Arg Ile Ala
                165                 170                 175 cgc atc gcg ttt gaa tct gct cgc aag cgt cgc cac aaa gtg acg tcg    576
Arg Ile Ala Phe Glu Ser Ala Arg Lys Arg Arg His Lys Val Thr Ser
            180                 185                 190 atc gat aaa gcc aac gtg ctg caa tcc tct att tta tgg cgg gag atc    624
Ile Asp Lys Ala Asn Val Leu Gln Ser Ser Ile Leu Trp Arg Glu Ile
        195                 200                 205 gtt aac gag atc gcc acg gaa tac ccg gat gtc gaa ctg gcg cac atg    672
Val Asn Glu Ile Ala Thr Glu Tyr Pro Asp Val Glu Leu Ala His Met
    210                 215                 220 tac atc gac aac gcc acc atg cag ctg att aaa gat cca tca cag ttt    720
Tyr Ile Asp Asn Ala Thr Met Gln Leu Ile Lys Asp Pro Ser Gln Phe
225                 230                 235                 240 gac gtt ctg ctg tgc tcc aac ctg ttt ggc gac att ctg tct gac gag    768
Asp Val Leu Leu Cys Ser Asn Leu Phe Gly Asp Ile Leu Ser Asp Glu
                245                 250                 255 tgc gca atg atc act ggc tcg atg ggg atg ttg cct tcc gcc agc ctg    816
Cys Ala Met Ile Thr Gly Ser Met Gly Met Leu Pro Ser Ala Ser Leu
            260                 265                 270 aac gag caa ggt ttt gga ctg tat gaa ccg gcg ggc ggc tcg gca cca    864
Asn Glu Gln Gly Phe Gly Leu Tyr Glu Pro Ala Gly Gly Ser Ala Pro
        275                 280                 285 gat atc gca ggc aaa aac atc gcc aac ccg att gca caa atc ctt tcg    912
Asp Ile Ala Gly Lys Asn Ile Ala Asn Pro Ile Ala Gln Ile Leu Ser
    290                 295                 300 ctg gca ctg ctg ctg cgt tac agc ctg gat gcc gat gat gcg gct tgc    960
Leu Ala Leu Leu Leu Arg Tyr Ser Leu Asp Ala Asp Asp Ala Ala Cys
305                 310                 315                 320 gcc att gaa cgc gcc att aac cgc gca tta gaa gaa ggc att cgc acc   1008
Ala Ile Glu Arg Ala Ile Asn Arg Ala Leu Glu Glu Gly Ile Arg Thr
                325                 330                 335 ggg gat tta gcc cgt ggc gct gcc gcc gtt agt acc gat gaa atg ggc   1056
Gly Asp Leu Ala Arg Gly Ala Ala Ala Val Ser Thr Asp Glu Met Gly
            340                 345                 350 gat atc att gcc cgc tat gta gca gaa ggg gtg                       1089
Asp Ile Ile Ala Arg Tyr Val Ala Glu Gly Val
        355                 360
```

<210> SEQ ID NO 4
<211> LENGTH: 363
<212> TYPE: PRT
<213> ORGANISM: Artificial Sequence
<220> FEATURE:
<223> OTHER INFORMATION: Synthetic Construct

<400> SEQUENCE: 4

```
Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
            20                  25                  30
```

Arg Phe Ala Met Arg Ile Thr Thr Ser His Tyr Asp Val Gly Gly Ala
          35                  40                  45

Ala Ile Asp Asn His Gly Gln Pro Leu Pro Pro Ala Thr Val Glu Gly
 50                  55                  60

Cys Glu Gln Ala Asp Ala Val Leu Phe Gly Ser Val Gly Gly Pro Lys
 65                  70                  75                  80

Trp Glu His Leu Pro Pro Asp Gln Gln Pro Glu Arg Gly Ala Leu Ala
                 85                  90                  95

Pro Leu Arg Lys His Phe Lys Leu Phe Ser Asn Leu Arg Pro Ala Lys
                100                 105                 110

Leu Tyr Gln Gly Leu Glu Ala Phe Cys Pro Leu Arg Ala Asp Ile Ala
            115                 120                 125

Ala Asn Gly Phe Asp Ile Leu Cys Val Arg Glu Leu Thr Gly Gly Ile
        130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg Arg His Lys Val Thr Ser
            180                 185                 190

Ile Asp Lys Ala Asn Val Leu Gln Ser Ser Ile Leu Trp Arg Glu Ile
        195                 200                 205

Val Asn Glu Ile Ala Thr Glu Tyr Pro Asp Val Glu Leu Ala His Met
210                 215                 220

Tyr Ile Asp Asn Ala Thr Met Gln Leu Ile Lys Asp Pro Ser Gln Phe
225                 230                 235                 240

Asp Val Leu Leu Cys Ser Asn Leu Phe Gly Asp Ile Leu Ser Asp Glu
                245                 250                 255

Cys Ala Met Ile Thr Gly Ser Met Gly Met Leu Pro Ser Ala Ser Leu
            260                 265                 270

Asn Glu Gln Gly Phe Gly Leu Tyr Glu Pro Ala Gly Gly Ser Ala Pro
        275                 280                 285

Asp Ile Ala Gly Lys Asn Ile Ala Asn Pro Ile Ala Gln Ile Leu Ser
        290                 295                 300

Leu Ala Leu Leu Leu Arg Tyr Ser Leu Asp Ala Asp Ala Ala Cys
305                 310                 315                 320

Ala Ile Glu Arg Ala Ile Asn Arg Ala Leu Glu Glu Gly Ile Arg Thr
                325                 330                 335

Gly Asp Leu Ala Arg Gly Ala Ala Val Ser Thr Asp Glu Met Gly
            340                 345                 350

Asp Ile Ile Ala Arg Tyr Val Ala Glu Gly Val
        355                 360

<210> SEQ ID NO 5
<211> LENGTH: 1089
<212> TYPE: DNA
<213> ORGANISM: Artificial Sequence
<220> FEATURE:
<223> OTHER INFORMATION: Synthesized - SEQ ID NO:3 L96V
<220> FEATURE:
<221> NAME/KEY: CDS
<222> LOCATION: (1)..(1089)
<220> FEATURE:
<221> NAME/KEY: mat_peptide
<222> LOCATION: (1)..(1089)
<220> FEATURE:
<221> NAME/KEY: gene

<222> LOCATION: (1)..(1089)
<223> OTHER INFORMATION: SEQ ID NO:3 L96V

<400> SEQUENCE: 5

```
atg tcg aag aat tac cat att gcc gta ttg ccg ggg gac ggt att ggt      48
Met Ser Lys Asn Tyr His Ile Ala Val Leu Pro Gly Asp Gly Ile Gly
1               5                   10                  15 ccg gaa gtg atg acc cag gcg ctg aaa gtg ctg gat gcc gtg cgc aac      96
Pro Glu Val Met Thr Gln Ala Leu Lys Val Leu Asp Ala Val Arg Asn
            20                  25                  30 cgc ttt gcg atg cgc atc acc acc agc cat tac gat gta ggc ggc gca     144
Arg Phe Ala Met Arg Ile Thr Thr Ser His Tyr Asp Val Gly Gly Ala
        35                  40                  45 gcc att gat aac cac ggg caa cca ctg ccg cct gcg acg gtt gaa ggt     192
Ala Ile Asp Asn His Gly Gln Pro Leu Pro Pro Ala Thr Val Glu Gly
50                  55                  60 tgt gag caa gcc gat gcc gtg ctg ttt ggc tcg gta ggc ggc ccg aag     240
Cys Glu Gln Ala Asp Ala Val Leu Phe Gly Ser Val Gly Gly Pro Lys
65                  70                  75                  80 tgg gaa cat tta cca cca gac cag caa cca gaa cgc ggc gcg ctg gtg     288
Trp Glu His Leu Pro Pro Asp Gln Gln Pro Glu Arg Gly Ala Leu Val
                85                  90                  95 cct ctg cgt aag cac ttc aaa tta ttc agc aac ctg cgc ccg gca aaa     336
Pro Leu Arg Lys His Phe Lys Leu Phe Ser Asn Leu Arg Pro Ala Lys
            100                 105                 110 ctg tat cag ggg ctg gaa gca ttc tgt ccg ctg cgt gca gac att gcc     384
Leu Tyr Gln Gly Leu Glu Ala Phe Cys Pro Leu Arg Ala Asp Ile Ala
        115                 120                 125 gca aac ggc ttc gac atc ctg tgt gtg cgc gaa ctg acc ggc ggc atc     432
Ala Asn Gly Phe Asp Ile Leu Cys Val Arg Glu Leu Thr Gly Gly Ile
130                 135                 140 tat ttc ggt cag cca aaa ggc cgc gaa ggt agc gga caa tat gaa aaa     480
Tyr Phe Gly Gln Pro Lys Gly Arg Glu Gly Ser Gly Gln Tyr Glu Lys
145                 150                 155                 160 gcc ttt gat acc gag gtg tat cac cgt ttt gag atc gaa cgt atc gcc     528
Ala Phe Asp Thr Glu Val Tyr His Arg Phe Glu Ile Glu Arg Ile Ala
                165                 170                 175 cgc atc gcg ttt gaa tct gct cgc aag cgt cgc cac aaa gtg acg tcg     576
Arg Ile Ala Phe Glu Ser Ala Arg Lys Arg Arg His Lys Val Thr Ser
            180                 185                 190 atc gat aaa gcc aac gtg ctg caa tcc tct att tta tgg cgg gag atc     624
Ile Asp Lys Ala Asn Val Leu Gln Ser Ser Ile Leu Trp Arg Glu Ile
        195                 200                 205 gtt aac gag atc gcc acg gaa tac ccg gat gtc gaa ctg gcg cac atg     672
Val Asn Glu Ile Ala Thr Glu Tyr Pro Asp Val Glu Leu Ala His Met
210                 215                 220 tac atc gac aac gcc acc atg cag ctg att aaa gat cca tca cag ttt     720
Tyr Ile Asp Asn Ala Thr Met Gln Leu Ile Lys Asp Pro Ser Gln Phe
225                 230                 235                 240 gac gtt ctg ctg tgc tcc aac ctg ttt ggc gac att ctg tct gac gag     768
Asp Val Leu Leu Cys Ser Asn Leu Phe Gly Asp Ile Leu Ser Asp Glu
                245                 250                 255 tgc gca atg atc act ggc tcg atg ggg atg ttg cct tcc gcc agc ctg     816
Cys Ala Met Ile Thr Gly Ser Met Gly Met Leu Pro Ser Ala Ser Leu
            260                 265                 270 aac gag caa ggt ttt gga ctg tat gaa ccg gcg ggc ggc tcg gca cca     864
Asn Glu Gln Gly Phe Gly Leu Tyr Glu Pro Ala Gly Gly Ser Ala Pro
        275                 280                 285 gat atc gca ggc aaa aac atc gcc aac ccg att gca caa atc ctt tcg     912
Asp Ile Ala Gly Lys Asn Ile Ala Asn Pro Ile Ala Gln Ile Leu Ser
```

```
                        290                 295                 300
ctg gca ctg ctg ctg cgt tac agc ctg gat gcc gat gat gcg gct tgc      960
Leu Ala Leu Leu Leu Arg Tyr Ser Leu Asp Ala Asp Asp Ala Ala Cys
305                 310                 315                 320 gcc att gaa cgc gcc att aac cgc gca tta gaa gaa ggc att cgc acc     1008
Ala Ile Glu Arg Ala Ile Asn Arg Ala Leu Glu Glu Gly Ile Arg Thr
                325                 330                 335 ggg gat tta gcc cgt ggc gct gcc gcc gtt agt acc gat gaa atg ggc     1056
Gly Asp Leu Ala Arg Gly Ala Ala Ala Val Ser Thr Asp Glu Met Gly
            340                 345                 350 gat atc att gcc cgc tat gta gca gaa ggg gtg                         1089
Asp Ile Ile Ala Arg Tyr Val Ala Glu Gly Val
            355                 360

<210> SEQ ID NO 6
<211> LENGTH: 363
<212> TYPE: PRT
<213> ORGANISM: Artificial Sequence
<220> FEATURE:
<223> OTHER INFORMATION: Synthetic Construct

<400> SEQUENCE: 6

Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
                20                  25                  30

Arg Phe Ala Met Arg Ile Thr Thr Ser His Tyr Asp Val Gly Gly Ala
            35                  40                  45

Ala Ile Asp Asn His Gly Gln Pro Leu Pro Pro Ala Thr Val Glu Gly
        50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Val
                85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
        115                 120                 125

Ala Asn Gly Phe Asp Ile Leu Cys Val Arg Glu Leu Thr Gly Gly Ile
    130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg Arg His Lys Val Thr Ser
            180                 185                 190

Ile Asp Lys Ala Asn Val Leu Gln Ser Ser Ile Leu Trp Arg Glu Ile
        195                 200                 205

Val Asn Glu Ile Ala Thr Glu Tyr Pro Asp Val Glu Leu Ala His Met
    210                 215                 220

Tyr Ile Asp Asn Ala Thr Met Gln Leu Ile Lys Asp Pro Ser Gln Phe
225                 230                 235                 240

Asp Val Leu Leu Cys Ser Asn Leu Phe Gly Asp Ile Leu Ser Asp Glu
                245                 250                 255

Cys Ala Met Ile Thr Gly Ser Met Gly Met Leu Pro Ser Ala Ser Leu
            260                 265                 270
```

```
Asn Glu Gln Gly Phe Gly Leu Tyr Glu Pro Ala Gly Ser Ala Pro
        275                 280                 285

Asp Ile Ala Gly Lys Asn Ile Ala Asn Pro Ile Ala Gln Ile Leu Ser
290                 295                 300

Leu Ala Leu Leu Leu Arg Tyr Ser Leu Asp Ala Asp Ala Ala Cys
305                 310                 315                 320

Ala Ile Glu Arg Ala Ile Asn Arg Ala Leu Glu Gly Ile Arg Thr
                325                 330                 335

Gly Asp Leu Ala Arg Gly Ala Ala Val Ser Thr Asp Glu Met Gly
                340                 345                 350

Asp Ile Ile Ala Arg Tyr Val Ala Glu Gly Val
                355                 360

<210> SEQ ID NO 7
<211> LENGTH: 1089
<212> TYPE: DNA
<213> ORGANISM: Artificial Sequence
<220> FEATURE:
<223> OTHER INFORMATION: SEQ ID NO:4 L96G
<220> FEATURE:
<221> NAME/KEY: CDS
<222> LOCATION: (1)..(1089)
<220> FEATURE:
<221> NAME/KEY: mat_peptide
<222> LOCATION: (1)..(1089)
<220> FEATURE:
<221> NAME/KEY: gene
<222> LOCATION: (1)..(1089)
<223> OTHER INFORMATION: SEQ ID NO:4 L96G

<400> SEQUENCE: 7 atg tcg aag aat tac cat att gcc gta ttg ccg ggg gac ggt att ggt    48
Met Ser Lys Asn Tyr His Ile Ala Val Leu Pro Gly Asp Gly Ile Gly
1               5                   10                  15 ccg gaa gtg atg acc cag gcg ctg aaa gtg ctg gat gcc gtg cgc aac    96
Pro Glu Val Met Thr Gln Ala Leu Lys Val Leu Asp Ala Val Arg Asn
                20                  25                  30 cgc ttt gcg atg cgc atc acc acc agc cat tac gat gta ggc ggc gca   144
Arg Phe Ala Met Arg Ile Thr Thr Ser His Tyr Asp Val Gly Gly Ala
            35                  40                  45 gcc att gat aac cac ggg caa cca ctg ccg cct gcg acg gtt gaa ggt   192
Ala Ile Asp Asn His Gly Gln Pro Leu Pro Pro Ala Thr Val Glu Gly
    50                  55                  60 tgt gag caa gcc gat gcc gtg ctg ttt ggc tcg gta ggc ggc ccg aag   240
Cys Glu Gln Ala Asp Ala Val Leu Phe Gly Ser Val Gly Gly Pro Lys
65                  70                  75                  80 tgg gaa cat tta cca cca gac cag caa cca gaa cgc ggc gcg ctg ggt   288
Trp Glu His Leu Pro Pro Asp Gln Gln Pro Glu Arg Gly Ala Leu Gly
                85                  90                  95 cct ctg cgt aag cac ttc aaa tta ttc agc aac ctg cgc ccg gca aaa   336
Pro Leu Arg Lys His Phe Lys Leu Phe Ser Asn Leu Arg Pro Ala Lys
            100                 105                 110 ctg tat cag ggg ctg gaa gca ttc tgt ccg ctg cgt gca gac att gcc   384
Leu Tyr Gln Gly Leu Glu Ala Phe Cys Pro Leu Arg Ala Asp Ile Ala
    115                 120                 125 gca aac ggc ttc gac atc ctg tgt gtg cgc gaa ctg acc ggc ggc atc   432
Ala Asn Gly Phe Asp Ile Leu Cys Val Arg Glu Leu Thr Gly Gly Ile
130                 135                 140 tat ttc ggt cag cca aaa ggc gcc gaa ggt agc gga caa tat gaa aaa   480
Tyr Phe Gly Gln Pro Lys Gly Arg Glu Gly Ser Gly Gln Tyr Glu Lys
145                 150                 155                 160 gcc ttt gat acc gag gtg tat cac cgt ttt gag atc gaa cgt atc gcc   528
Ala Phe Asp Thr Glu Val Tyr His Arg Phe Glu Ile Glu Arg Ile Ala
```

```
                Ala Phe Asp Thr Glu Val Tyr His Arg Phe Glu Ile Glu Arg Ile Ala
                                165                 170                 175 cgc atc gcg ttt gaa tct gct cgc aag cgt cgc cac aaa gtg acg tcg         576
Arg Ile Ala Phe Glu Ser Ala Arg Lys Arg Arg His Lys Val Thr Ser
            180                 185                 190 atc gat aaa gcc aac gtg ctg caa tcc tct att tta tgg cgg gag atc         624
Ile Asp Lys Ala Asn Val Leu Gln Ser Ser Ile Leu Trp Arg Glu Ile
        195                 200                 205 gtt aac gag atc gcc acg gaa tac ccg gat gtc gaa ctg gcg cac atg         672
Val Asn Glu Ile Ala Thr Glu Tyr Pro Asp Val Glu Leu Ala His Met
    210                 215                 220 tac atc gac aac gcc acc atg cag ctg att aaa gat cca tca cag ttt         720
Tyr Ile Asp Asn Ala Thr Met Gln Leu Ile Lys Asp Pro Ser Gln Phe
225                 230                 235                 240 gac gtt ctg ctg tgc tcc aac ctg ttt ggc gac att ctg tct gac gag         768
Asp Val Leu Leu Cys Ser Asn Leu Phe Gly Asp Ile Leu Ser Asp Glu
                245                 250                 255 tgc gca atg atc act ggc tcg atg ggg atg ttg cct tcc gcc agc ctg         816
Cys Ala Met Ile Thr Gly Ser Met Gly Met Leu Pro Ser Ala Ser Leu
            260                 265                 270 aac gag caa ggt ttt gga ctg tat gaa ccg gcg ggc ggc tcg gca cca         864
Asn Glu Gln Gly Phe Gly Leu Tyr Glu Pro Ala Gly Gly Ser Ala Pro
        275                 280                 285 gat atc gca ggc aaa aac atc gcc aac ccg att gca caa atc ctt tcg         912
Asp Ile Ala Gly Lys Asn Ile Ala Asn Pro Ile Ala Gln Ile Leu Ser
    290                 295                 300 ctg gca ctg ctg ctg cgt tac agc ctg gat gcc gat gat gcg gct tgc         960
Leu Ala Leu Leu Leu Arg Tyr Ser Leu Asp Ala Asp Asp Ala Ala Cys
305                 310                 315                 320 gcc att gaa cgc gcc att aac cgc gca tta gaa gaa ggc att cgc acc        1008
Ala Ile Glu Arg Ala Ile Asn Arg Ala Leu Glu Glu Gly Ile Arg Thr
                325                 330                 335 ggg gat tta gcc cgt ggc gct gcc gcc gtt agt acc gat gaa atg ggc        1056
Gly Asp Leu Ala Arg Gly Ala Ala Ala Val Ser Thr Asp Glu Met Gly
            340                 345                 350 gat atc att gcc cgc tat gta gca gaa ggg gtg                            1089
Asp Ile Ile Ala Arg Tyr Val Ala Glu Gly Val
        355                 360

<210> SEQ ID NO 8
<211> LENGTH: 363
<212> TYPE: PRT
<213> ORGANISM: Artificial Sequence
<220> FEATURE:
<223> OTHER INFORMATION: Synthetic Construct

<400> SEQUENCE: 8

Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
            20                  25                  30

Arg Phe Ala Met Arg Ile Thr Thr Ser His Tyr Asp Val Gly Gly Ala
        35                  40                  45

Ala Ile Asp Asn His Gly Gln Pro Leu Pro Ala Thr Val Glu Gly
    50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Gly
                85                  90                  95
```

-continued

```
            Pro Leu Arg Lys His Phe Lys Leu Phe Ser Asn Leu Arg Pro Ala Lys
                        100                 105                 110

Leu Tyr Gln Gly Leu Glu Ala Phe Cys Pro Leu Arg Ala Asp Ile Ala
                    115                 120                 125

Ala Asn Gly Phe Asp Ile Leu Cys Val Arg Glu Leu Thr Gly Gly Ile
                130                 135                 140

Tyr Phe Gly Gln Pro Lys Gly Arg Glu Gly Ser Gly Gln Tyr Glu Lys
            145                 150                 155                 160

Ala Phe Asp Thr Glu Val Tyr His Arg Phe Ile Glu Arg Ile Ala
                            165                 170                 175

Arg Ile Ala Phe Glu Ser Ala Arg Lys Arg His Lys Val Thr Ser
                        180                 185                 190

Ile Asp Lys Ala Asn Val Leu Gln Ser Ser Ile Leu Trp Arg Glu Ile
                    195                 200                 205

Val Asn Glu Ile Ala Thr Glu Tyr Pro Asp Val Glu Leu Ala His Met
                210                 215                 220

Tyr Ile Asp Asn Ala Thr Met Gln Leu Ile Lys Asp Pro Ser Gln Phe
            225                 230                 235                 240

Asp Val Leu Leu Cys Ser Asn Leu Phe Gly Asp Ile Leu Ser Asp Glu
                            245                 250                 255

Cys Ala Met Ile Thr Gly Ser Met Gly Met Leu Pro Ser Ala Ser Leu
                        260                 265                 270

Asn Glu Gln Gly Phe Gly Leu Tyr Glu Pro Ala Gly Ser Ala Pro
                    275                 280                 285

Asp Ile Ala Gly Lys Asn Ile Ala Asn Pro Ile Ala Gln Ile Leu Ser
                290                 295                 300

Leu Ala Leu Leu Leu Arg Tyr Ser Leu Asp Ala Asp Ala Ala Cys
            305                 310                 315                 320

Ala Ile Glu Arg Ala Ile Asn Arg Ala Leu Glu Gly Ile Arg Thr
                            325                 330                 335

Gly Asp Leu Ala Arg Gly Ala Ala Ala Val Ser Thr Asp Glu Met Gly
                        340                 345                 350

Asp Ile Ile Ala Arg Tyr Val Ala Glu Gly Val
                    355                 360

<210> SEQ ID NO 9
<211> LENGTH: 1089
<212> TYPE: DNA
<213> ORGANISM: Artificial Sequence
<220> FEATURE:
<223> OTHER INFORMATION: Synthesized - SEQ ID NO:5 V198A
<220> FEATURE:
<221> NAME/KEY: CDS
<222> LOCATION: (1)..(1089)
<220> FEATURE:
<221> NAME/KEY: mat_peptide
<222> LOCATION: (1)..(1089)
<220> FEATURE:
<221> NAME/KEY: gene
<222> LOCATION: (1)..(1089)
<223> OTHER INFORMATION: SEQ ID NO:5 V198A

<400> SEQUENCE: 9 atg tcg aag aat tac cat att gcc gta ttg ccg ggg gac ggt att ggt       48
Met Ser Lys Asn Tyr His Ile Ala Val Leu Pro Gly Asp Gly Ile Gly
  1               5                  10                  15 ccg gaa gtg atg acc cag gcg ctg aaa gtg ctg gat gcc gtg cgc aac       96
Pro Glu Val Met Thr Gln Ala Leu Lys Val Leu Asp Ala Val Arg Asn
             20                  25                  30
```

-continued

| | |
|---|---|
| cgc ttt gcg atg cgc atc acc acc agc cat tac gat gta ggc ggc gca<br>Arg Phe Ala Met Arg Ile Thr Thr Ser His Tyr Asp Val Gly Gly Ala<br>                35                        40                      45 | 144 |
| gcc att gat aac cac ggg caa cca ctg ccg cct gcg acg gtt gaa ggt<br>Ala Ile Asp Asn His Gly Gln Pro Leu Pro Pro Ala Thr Val Glu Gly<br>50                              55                        60 | 192 |
| tgt gag caa gcc gat gcc gtg ctg ttt ggc tcg gta ggc ggc ccg aag<br>Cys Glu Gln Ala Asp Ala Val Leu Phe Gly Ser Val Gly Gly Pro Lys<br>65                              70                        75                        80 | 240 |
| tgg gaa cat tta cca cca gac cag caa cca gaa cgc ggc gcg ctg ctg<br>Trp Glu His Leu Pro Pro Asp Gln Gln Pro Glu Arg Gly Ala Leu Leu<br>                85                                  90                        95 | 288 |
| cct ctg cgt aag cac ttc aaa tta ttc agc aac ctg cgc ccg gca aaa<br>Pro Leu Arg Lys His Phe Lys Leu Phe Ser Asn Leu Arg Pro Ala Lys<br>                    100                        105                        110 | 336 |
| ctg tat cag ggg ctg gaa gca ttc tgt ccg ctg cgt gca gac att gcc<br>Leu Tyr Gln Gly Leu Glu Ala Phe Cys Pro Leu Arg Ala Asp Ile Ala<br>                115                        120                        125 | 384 |
| gca aac ggc ttc gac atc ctg tgt gtg cgc gaa ctg acc ggc ggc atc<br>Ala Asn Gly Phe Asp Ile Leu Cys Val Arg Glu Leu Thr Gly Gly Ile<br>130                              135                        140 | 432 |
| tat ttc ggt cag cca aaa ggc cgc gaa ggt agc gga caa tat gaa aaa<br>Tyr Phe Gly Gln Pro Lys Gly Arg Glu Gly Ser Gly Gln Tyr Glu Lys<br>145                            150                        155                        160 | 480 |
| gcc ttt gat acc gag gtg tat cac cgt ttt gag atc gaa cgt atc gcc<br>Ala Phe Asp Thr Glu Val Tyr His Arg Phe Glu Ile Glu Arg Ile Ala<br>                165                        170                        175 | 528 |
| cgc atc gcg ttt gaa tct gct cgc aag cgt cgc cac aaa gtg acg tcg<br>Arg Ile Ala Phe Glu Ser Ala Arg Lys Arg Arg His Lys Val Thr Ser<br>                    180                        185                        190 | 576 |
| atc gat aaa gcc aac gcg ctg caa tcc tct att tta tgg cgg gag atc<br>Ile Asp Lys Ala Asn Ala Leu Gln Ser Ser Ile Leu Trp Arg Glu Ile<br>195                              200                        205 | 624 |
| gtt aac gag atc gcc acg gaa tac ccg gat gtc gaa ctg gcg cac atg<br>Val Asn Glu Ile Ala Thr Glu Tyr Pro Asp Val Glu Leu Ala His Met<br>210                              215                        220 | 672 |
| tac atc gac aac gcc acc atg cag ctg att aaa gat cca tca cag ttt<br>Tyr Ile Asp Asn Ala Thr Met Gln Leu Ile Lys Asp Pro Ser Gln Phe<br>225                              230                        235                        240 | 720 |
| gac gtt ctg ctg tgc tcc aac ctg ttt ggc gac att ctg tct gac gag<br>Asp Val Leu Leu Cys Ser Asn Leu Phe Gly Asp Ile Leu Ser Asp Glu<br>                              245                        250                        255 | 768 |
| tgc gca atg atc act ggc tcg atg ggg atg ttg cct tcc gcc agc ctg<br>Cys Ala Met Ile Thr Gly Ser Met Gly Met Leu Pro Ser Ala Ser Leu<br>260                              265                        270 | 816 |
| aac gag caa ggt ttt gga ctg tat gaa ccg gcg ggc ggc tcg gca cca<br>Asn Glu Gln Gly Phe Gly Leu Tyr Glu Pro Ala Gly Gly Ser Ala Pro<br>                275                        280                        285 | 864 |
| gat atc gca ggc aaa aac atc gcc aac ccg att gca caa atc ctt tcg<br>Asp Ile Ala Gly Lys Asn Ile Ala Asn Pro Ile Ala Gln Ile Leu Ser<br>290                              295                        300 | 912 |
| ctg gca ctg ctg ctg cgt tac agc ctg gat gcc gat gat gcg gct tgc<br>Leu Ala Leu Leu Leu Arg Tyr Ser Leu Asp Ala Asp Asp Ala Ala Cys<br>305                              310                        315                        320 | 960 |
| gcc att gaa cgc gcc att aac cgc gca tta gaa gaa ggc att cgc acc<br>Ala Ile Glu Arg Ala Ile Asn Arg Ala Leu Glu Glu Gly Ile Arg Thr<br>                325                        330                        335 | 1008 |
| ggg gat tta gcc cgt ggc gct gcc gcc gtt agt acc gat gaa atg ggc<br>Gly Asp Leu Ala Arg Gly Ala Ala Ala Val Ser Thr Asp Glu Met Gly<br>                    340                        345                        350 | 1056 |

```
gat atc att gcc cgc tat gta gca gaa ggg gtg                      1089
Asp Ile Ile Ala Arg Tyr Val Ala Glu Gly Val
        355                 360
```

<210> SEQ ID NO 10
<211> LENGTH: 363
<212> TYPE: PRT
<213> ORGANISM: Artificial Sequence
<220> FEATURE:
<223> OTHER INFORMATION: Synthetic Construct

<400> SEQUENCE: 10

```
Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
            20                  25                  30

Arg Phe Ala Met Arg Ile Thr Thr Ser His Tyr Asp Val Gly Gly Ala
        35                  40                  45

Ala Ile Asp Asn His Gly Gln Pro Leu Pro Pro Ala Thr Val Glu Gly
    50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Leu
                85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
        115                 120                 125

Ala Asn Gly Phe Asp Ile Leu Cys Val Arg Glu Leu Thr Gly Gly Ile
    130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg Arg His Lys Val Thr Ser
            180                 185                 190

Ile Asp Lys Ala Asn Ala Leu Gln Ser Ser Ile Leu Trp Arg Glu Ile
        195                 200                 205

Val Asn Glu Ile Ala Thr Glu Tyr Pro Asp Val Glu Leu Ala His Met
    210                 215                 220

Tyr Ile Asp Asn Ala Thr Met Gln Leu Ile Lys Asp Pro Ser Gln Phe
225                 230                 235                 240

Asp Val Leu Leu Cys Ser Asn Leu Phe Gly Asp Ile Leu Ser Asp Glu
                245                 250                 255

Cys Ala Met Ile Thr Gly Ser Met Gly Met Leu Pro Ser Ala Ser Leu
            260                 265                 270

Asn Glu Gln Gly Phe Gly Leu Tyr Glu Pro Ala Gly Gly Ser Ala Pro
        275                 280                 285

Asp Ile Ala Gly Lys Asn Ile Ala Asn Pro Ile Ala Gln Ile Leu Ser
    290                 295                 300

Leu Ala Leu Leu Leu Arg Tyr Ser Leu Asp Ala Asp Ala Ala Cys
305                 310                 315                 320

Ala Ile Glu Arg Ala Ile Asn Arg Ala Leu Glu Glu Gly Ile Arg Thr
                325                 330                 335

Gly Asp Leu Ala Arg Gly Ala Ala Ala Val Ser Thr Asp Glu Met Gly
```

-continued

```
                    340                 345                 350
Asp Ile Ile Ala Arg Tyr Val Ala Glu Gly Val
                355                 360

<210> SEQ ID NO 11
<211> LENGTH: 1089
<212> TYPE: DNA
<213> ORGANISM: Artificial Sequence
<220> FEATURE:
<223> OTHER INFORMATION: Synthesized - SEQ ID NO:6 V198G
<220> FEATURE:
<221> NAME/KEY: CDS
<222> LOCATION: (1)..(1089)
<220> FEATURE:
<221> NAME/KEY: mat_peptide
<222> LOCATION: (1)..(1089)
<220> FEATURE:
<221> NAME/KEY: gene
<222> LOCATION: (1)..(1089)
<223> OTHER INFORMATION: SEQ ID NO:6 V198G

<400> SEQUENCE: 11 atg tcg aag aat tac cat att gcc gta ttg ccg ggg gac ggt att ggt      48
Met Ser Lys Asn Tyr His Ile Ala Val Leu Pro Gly Asp Gly Ile Gly
1               5                  10                  15 ccg gaa gtg atg acc cag gcg ctg aaa gtg ctg gat gcc gtg cgc aac      96
Pro Glu Val Met Thr Gln Ala Leu Lys Val Leu Asp Ala Val Arg Asn
            20                  25                  30 cgc ttt gcg atg cgc atc acc acc agc cat tac gat gta ggc ggc gca     144
Arg Phe Ala Met Arg Ile Thr Thr Ser His Tyr Asp Val Gly Gly Ala
        35                  40                  45 gcc att gat aac cac ggg caa cca ctg ccg cct gcg acg gtt gaa ggt     192
Ala Ile Asp Asn His Gly Gln Pro Leu Pro Pro Ala Thr Val Glu Gly
    50                  55                  60 tgt gag caa gcc gat gcc gtg ctg ttt ggc tcg gta ggc ggc ccg aag     240
Cys Glu Gln Ala Asp Ala Val Leu Phe Gly Ser Val Gly Gly Pro Lys
65                  70                  75                  80 tgg gaa cat tta cca cca gac cag caa cca gaa cgc ggc gcg ctg ctg     288
Trp Glu His Leu Pro Pro Asp Gln Gln Pro Glu Arg Gly Ala Leu Leu
                85                  90                  95 cct ctg cgt aag cac ttc aaa tta ttc agc aac ctg cgc ccg gca aaa     336
Pro Leu Arg Lys His Phe Lys Leu Phe Ser Asn Leu Arg Pro Ala Lys
            100                 105                 110 ctg tat cag ggg ctg gaa gca ttc tgt ccg ctg cgt gca gac att gcc     384
Leu Tyr Gln Gly Leu Glu Ala Phe Cys Pro Leu Arg Ala Asp Ile Ala
        115                 120                 125 gca aac ggc ttc gac atc ctg tgt gtg cgc gaa ctg acc ggc ggc atc     432
Ala Asn Gly Phe Asp Ile Leu Cys Val Arg Glu Leu Thr Gly Gly Ile
    130                 135                 140 tat ttc ggt cag cca aaa ggc gcg gaa ggt agc gga caa tat gaa aaa     480
Tyr Phe Gly Gln Pro Lys Gly Arg Glu Gly Ser Gly Gln Tyr Glu Lys
145                 150                 155                 160 gcc ttt gat acc gag gtg tat cac cgt ttt gag atc gaa cgt atc gcc     528
Ala Phe Asp Thr Glu Val Tyr His Arg Phe Glu Ile Glu Arg Ile Ala
                165                 170                 175 cgc atc gcg ttt gaa tct gct cgc aag cgt cgc cac aaa gtg acg tcg     576
Arg Ile Ala Phe Glu Ser Ala Arg Lys Arg Arg His Lys Val Thr Ser
            180                 185                 190 atc gat aaa gcc aac ggt ctg caa tcc tct att tta tgg cgg gag atc     624
Ile Asp Lys Ala Asn Gly Leu Gln Ser Ser Ile Leu Trp Arg Glu Ile
        195                 200                 205 gtt aac gag atc gcc acg gaa tac ccg gat gtc gaa ctg gcg cac atg     672
Val Asn Glu Ile Ala Thr Glu Tyr Pro Asp Val Glu Leu Ala His Met
    210                 215                 220
```

```
                      210                 215                 220
tac atc gac aac gcc acc atg cag ctg att aaa gat cca tca cag ttt       720
Tyr Ile Asp Asn Ala Thr Met Gln Leu Ile Lys Asp Pro Ser Gln Phe
225                 230                 235                 240 gac gtt ctg ctg tgc tcc aac ctg ttt ggc gac att ctg tct gac gag       768
Asp Val Leu Leu Cys Ser Asn Leu Phe Gly Asp Ile Leu Ser Asp Glu
                245                 250                 255 tgc gca atg atc act ggc tcg atg ggg atg ttg cct tcc gcc agc ctg       816
Cys Ala Met Ile Thr Gly Ser Met Gly Met Leu Pro Ser Ala Ser Leu
            260                 265                 270 aac gag caa ggt ttt gga ctg tat gaa ccg gcg ggc tcg gca cca           864
Asn Glu Gln Gly Phe Gly Leu Tyr Glu Pro Ala Gly Ser Ala Pro
        275                 280                 285 gat atc gca ggc aaa aac atc gcc aac ccg att gca caa atc ctt tcg       912
Asp Ile Ala Gly Lys Asn Ile Ala Asn Pro Ile Ala Gln Ile Leu Ser
290                 295                 300 ctg gca ctg ctg ctg cgt tac agc ctg gat gcc gat gat gcg gct tgc       960
Leu Ala Leu Leu Leu Arg Tyr Ser Leu Asp Ala Asp Asp Ala Ala Cys
305                 310                 315                 320 gcc att gaa cgc gcc att aac cgc gca tta gaa gaa ggc att cgc acc      1008
Ala Ile Glu Arg Ala Ile Asn Arg Ala Leu Glu Glu Gly Ile Arg Thr
                325                 330                 335 ggg gat tta gcc cgt ggc gct gcc gcc gtt agt acc gat gaa atg ggc      1056
Gly Asp Leu Ala Arg Gly Ala Ala Ala Val Ser Thr Asp Glu Met Gly
            340                 345                 350 gat atc att gcc cgc tat gta gca gaa ggg gtg                          1089
Asp Ile Ile Ala Arg Tyr Val Ala Glu Gly Val
        355                 360

<210> SEQ ID NO 12
<211> LENGTH: 363
<212> TYPE: PRT
<213> ORGANISM: Artificial Sequence
<220> FEATURE:
<223> OTHER INFORMATION: Synthetic Construct

<400> SEQUENCE: 12

Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
                20                  25                  30

Arg Phe Ala Met Arg Ile Thr Thr Ser His Tyr Asp Val Gly Gly Ala
            35                  40                  45

Ala Ile Asp Asn His Gly Gln Pro Leu Pro Ala Thr Val Glu Gly
        50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Leu
                85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
        115                 120                 125

Ala Asn Gly Phe Asp Ile Leu Cys Val Arg Glu Leu Thr Gly Gly Ile
    130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
```

-continued

```
                      165                 170                 175
Arg Ile Ala Phe Glu Ser Ala Arg Lys Arg His Lys Val Thr Ser
                180                 185                 190
Ile Asp Lys Ala Asn Gly Leu Gln Ser Ser Ile Leu Trp Arg Glu Ile
                195                 200                 205
Val Asn Glu Ile Ala Thr Glu Tyr Pro Asp Val Glu Leu Ala His Met
            210                 215                 220
Tyr Ile Asp Asn Ala Thr Met Gln Leu Ile Lys Asp Pro Ser Gln Phe
225                 230                 235                 240
Asp Val Leu Leu Cys Ser Asn Leu Phe Gly Asp Ile Leu Ser Asp Glu
                245                 250                 255
Cys Ala Met Ile Thr Gly Ser Met Gly Met Leu Pro Ser Ala Ser Leu
                260                 265                 270
Asn Glu Gln Gly Phe Gly Leu Tyr Glu Pro Ala Gly Gly Ser Ala Pro
                275                 280                 285
Asp Ile Ala Gly Lys Asn Ile Ala Asn Pro Ile Ala Gln Ile Leu Ser
            290                 295                 300
Leu Ala Leu Leu Leu Arg Tyr Ser Leu Asp Ala Asp Asp Ala Ala Cys
305                 310                 315                 320
Ala Ile Glu Arg Ala Ile Asn Arg Ala Leu Glu Glu Gly Ile Arg Thr
                325                 330                 335
Gly Asp Leu Ala Arg Gly Ala Ala Val Ser Thr Asp Glu Met Gly
                340                 345                 350
Asp Ile Ile Ala Arg Tyr Val Ala Glu Gly Val
            355                 360
```

<210> SEQ ID NO 13
<211> LENGTH: 1089
<212> TYPE: DNA
<213> ORGANISM: Artificial Sequence
<220> FEATURE:
<223> OTHER INFORMATION: Synthesized - SEQ ID NO:7 L96A/V198A
<220> FEATURE:
<221> NAME/KEY: CDS
<222> LOCATION: (1)..(1089)
<220> FEATURE:
<221> NAME/KEY: mat_peptide
<222> LOCATION: (1)..(1089)
<220> FEATURE:
<221> NAME/KEY: gene
<222> LOCATION: (1)..(1089)
<223> OTHER INFORMATION: SEQ ID NO:7 L96A/V198A

<400> SEQUENCE: 13

```
atg tcg aag aat tac cat att gcc gta ttg ccg ggg gac ggt att ggt      48
Met Ser Lys Asn Tyr His Ile Ala Val Leu Pro Gly Asp Gly Ile Gly
1               5                   10                  15 ccg gaa gtg atg acc cag gcg ctg aaa gtg ctg gat gcc gtg cgc aac      96
Pro Glu Val Met Thr Gln Ala Leu Lys Val Leu Asp Ala Val Arg Asn
            20                  25                  30 cgc ttt gcg atg cgc atc acc acc agc cat tac gat gta ggc ggc gca     144
Arg Phe Ala Met Arg Ile Thr Thr Ser His Tyr Asp Val Gly Gly Ala
        35                  40                  45 gcc att gat aac cac ggg caa cca ctg ccg cct gcg acg gtt gaa ggt     192
Ala Ile Asp Asn His Gly Gln Pro Leu Pro Pro Ala Thr Val Glu Gly
    50                  55                  60 tgt gag caa gcc gat gcc gtg ctg ttt ggc tcg gta ggc ggc ccg aag     240
Cys Glu Gln Ala Asp Ala Val Leu Phe Gly Ser Val Gly Gly Pro Lys
65                  70                  75                  80 tgg gaa cat tta cca cca gac cag caa cca gaa cgc ggc gcg ctg gcc     288
```

| | | | | | | | | | | | | |
|---|---|---|---|---|---|---|---|---|---|---|---|---|
| Trp | Glu | His | Leu | Pro | Pro | Asp | Gln | Gln | Pro | Glu | Arg | Gly | Ala | Leu | Ala |
| | | | | 85 | | | | | 90 | | | | | 95 | |

```
cct ctg cgt aag cac ttc aaa tta ttc agc aac ctg cgc ccg gca aaa       336
Pro Leu Arg Lys His Phe Lys Leu Phe Ser Asn Leu Arg Pro Ala Lys
            100                 105                 110 ctg tat cag ggg ctg gaa gca ttc tgt ccg ctg cgt gca gac att gcc       384
Leu Tyr Gln Gly Leu Glu Ala Phe Cys Pro Leu Arg Ala Asp Ile Ala
            115                 120                 125 gca aac ggc ttc gac atc ctg tgt gtg cgc gaa ctg acc ggc ggc atc       432
Ala Asn Gly Phe Asp Ile Leu Cys Val Arg Glu Leu Thr Gly Gly Ile
        130                 135                 140 tat ttc ggt cag cca aaa ggc cgc gaa ggt agc gga caa tat gaa aaa       480
Tyr Phe Gly Gln Pro Lys Gly Arg Glu Gly Ser Gly Gln Tyr Glu Lys
145                 150                 155                 160 gcc ttt gat acc gag gtg tat cac cgt ttt gag atc gaa cgt atc gcc       528
Ala Phe Asp Thr Glu Val Tyr His Arg Phe Glu Ile Glu Arg Ile Ala
                165                 170                 175 cgc atc gcg ttt gaa tct gct cgc aag cgt cgc cac aaa gtg acg tcg       576
Arg Ile Ala Phe Glu Ser Ala Arg Lys Arg Arg His Lys Val Thr Ser
            180                 185                 190 atc gat aaa gcc aac gcc ctg caa tcc tct att tta tgg cgg gag atc       624
Ile Asp Lys Ala Asn Ala Leu Gln Ser Ser Ile Leu Trp Arg Glu Ile
        195                 200                 205 gtt aac gag atc gcc acg gaa tac ccg gat gtc gaa ctg gcg cac atg       672
Val Asn Glu Ile Ala Thr Glu Tyr Pro Asp Val Glu Leu Ala His Met
210                 215                 220 tac atc gac aac gcc acc atg cag ctg att aaa gat cca tca cag ttt       720
Tyr Ile Asp Asn Ala Thr Met Gln Leu Ile Lys Asp Pro Ser Gln Phe
225                 230                 235                 240 gac gtt ctg ctg tgc tcc aac ctg ttt ggc gac att ctg tct gac gag       768
Asp Val Leu Leu Cys Ser Asn Leu Phe Gly Asp Ile Leu Ser Asp Glu
                245                 250                 255 tgc gca atg atc act ggc tcg atg ggg atg ttg cct tcc gcc agc ctg       816
Cys Ala Met Ile Thr Gly Ser Met Gly Met Leu Pro Ser Ala Ser Leu
            260                 265                 270 aac gag caa ggt ttt gga ctg tat gaa ccg gcg ggc ggc tcg gca cca       864
Asn Glu Gln Gly Phe Gly Leu Tyr Glu Pro Ala Gly Gly Ser Ala Pro
        275                 280                 285 gat atc gca ggc aaa aac atc gcc aac ccg att gca caa atc ctt tcg       912
Asp Ile Ala Gly Lys Asn Ile Ala Asn Pro Ile Ala Gln Ile Leu Ser
290                 295                 300 ctg gca ctg ctg ctg cgt tac agc ctg gat gcc gat gat gcg gct tgc       960
Leu Ala Leu Leu Leu Arg Tyr Ser Leu Asp Ala Asp Asp Ala Ala Cys
305                 310                 315                 320 gcc att gaa cgc gcc att aac cgc gca tta gaa gaa ggc att cgc acc      1008
Ala Ile Glu Arg Ala Ile Asn Arg Ala Leu Glu Glu Gly Ile Arg Thr
                325                 330                 335 ggg gat tta gcc cgt ggc gct gcc gcc gtt agt acc gat gaa atg ggc      1056
Gly Asp Leu Ala Arg Gly Ala Ala Ala Val Ser Thr Asp Glu Met Gly
            340                 345                 350 gat atc att gcc cgc tat gta gca gaa ggg gtg                          1089
Asp Ile Ile Ala Arg Tyr Val Ala Glu Gly Val
        355                 360

<210> SEQ ID NO 14
<211> LENGTH: 363
<212> TYPE: PRT
<213> ORGANISM: Artificial Sequence
<220> FEATURE:
<223> OTHER INFORMATION: Synthetic Construct
```

<400> SEQUENCE: 14

```
Met Ser Lys Asn Tyr His Ile Ala Val Leu Pro Gly Asp Gly Ile Gly
1               5                   10                  15
Pro Glu Val Met Thr Gln Ala Leu Lys Val Leu Asp Ala Val Arg Asn
            20                  25                  30
Arg Phe Ala Met Arg Ile Thr Thr Ser His Tyr Asp Val Gly Gly Ala
        35                  40                  45
Ala Ile Asp Asn His Gly Gln Pro Leu Pro Pro Ala Thr Val Glu Gly
    50                  55                  60
Cys Glu Gln Ala Asp Ala Val Leu Phe Gly Ser Val Gly Gly Pro Lys
65                  70                  75                  80
Trp Glu His Leu Pro Pro Asp Gln Gln Pro Glu Arg Gly Ala Leu Ala
                85                  90                  95
Pro Leu Arg Lys His Phe Lys Leu Phe Ser Asn Leu Arg Pro Ala Lys
            100                 105                 110
Leu Tyr Gln Gly Leu Glu Ala Phe Cys Pro Leu Arg Ala Asp Ile Ala
        115                 120                 125
Ala Asn Gly Phe Asp Ile Leu Cys Val Arg Glu Leu Thr Gly Gly Ile
    130                 135                 140
Tyr Phe Gly Gln Pro Lys Gly Arg Glu Gly Ser Gly Gln Tyr Glu Lys
145                 150                 155                 160
Ala Phe Asp Thr Glu Val Tyr His Arg Phe Glu Ile Glu Arg Ile Ala
                165                 170                 175
Arg Ile Ala Phe Glu Ser Ala Arg Lys Arg His Lys Val Thr Ser
            180                 185                 190
Ile Asp Lys Ala Asn Ala Leu Gln Ser Ser Ile Leu Trp Arg Glu Ile
        195                 200                 205
Val Asn Glu Ile Ala Thr Glu Tyr Pro Asp Val Glu Leu Ala His Met
    210                 215                 220
Tyr Ile Asp Asn Ala Thr Met Gln Leu Ile Lys Asp Pro Ser Gln Phe
225                 230                 235                 240
Asp Val Leu Leu Cys Ser Asn Leu Phe Gly Asp Ile Leu Ser Asp Glu
                245                 250                 255
Cys Ala Met Ile Thr Gly Ser Met Gly Met Leu Pro Ser Ala Ser Leu
            260                 265                 270
Asn Glu Gln Gly Phe Gly Leu Tyr Glu Pro Ala Gly Gly Ser Ala Pro
        275                 280                 285
Asp Ile Ala Gly Lys Asn Ile Ala Asn Pro Ile Ala Gln Ile Leu Ser
    290                 295                 300
Leu Ala Leu Leu Leu Arg Tyr Ser Leu Asp Ala Asp Ala Ala Cys
305                 310                 315                 320
Ala Ile Glu Arg Ala Ile Asn Arg Ala Leu Glu Glu Gly Ile Arg Thr
                325                 330                 335
Gly Asp Leu Ala Arg Gly Ala Ala Val Ser Thr Ala Glu Met Gly
            340                 345                 350
Asp Ile Ile Ala Arg Tyr Val Ala Glu Gly Val
        355                 360
```

<210> SEQ ID NO 15
<211> LENGTH: 1089
<212> TYPE: DNA
<213> ORGANISM: Artificial Sequence
<220> FEATURE:
<223> OTHER INFORMATION: Synthesized - SEQ ID NO:8 L96G/V198A
<220> FEATURE:

<221> NAME/KEY: CDS
<222> LOCATION: (1)..(1089)
<220> FEATURE:
<221> NAME/KEY: mat_peptide
<222> LOCATION: (1)..(1089)
<220> FEATURE:
<221> NAME/KEY: gene
<222> LOCATION: (1)..(1089)
<223> OTHER INFORMATION: SEQ ID NO:8 L96G/V198A

<400> SEQUENCE: 15

```
atg tcg aag aat tac cat att gcc gta ttg ccg ggg gac ggt att ggt     48
Met Ser Lys Asn Tyr His Ile Ala Val Leu Pro Gly Asp Gly Ile Gly
1               5                   10                  15 ccg gaa gtg atg acc cag gcg ctg aaa gtg ctg gat gcc gtg cgc aac     96
Pro Glu Val Met Thr Gln Ala Leu Lys Val Leu Asp Ala Val Arg Asn
            20                  25                  30 cgc ttt gcg atg cgc atc acc acc agc cat tac gat gta ggc ggc gca    144
Arg Phe Ala Met Arg Ile Thr Thr Ser His Tyr Asp Val Gly Gly Ala
        35                  40                  45 gcc att gat aac cac ggg caa cca ctg ccg cct gcg acg gtt gaa ggt    192
Ala Ile Asp Asn His Gly Gln Pro Leu Pro Pro Ala Thr Val Glu Gly
    50                  55                  60 tgt gag caa gcc gat gcc gtg ctg ttt ggc tcg gta ggc ggc ccg aag    240
Cys Glu Gln Ala Asp Ala Val Leu Phe Gly Ser Val Gly Gly Pro Lys
65                  70                  75                  80 tgg gaa cat tta cca cca gac cag caa cca gaa cgc ggc gcg ctg ggt    288
Trp Glu His Leu Pro Pro Asp Gln Gln Pro Glu Arg Gly Ala Leu Gly
                85                  90                  95 cct ctg cgt aag cac ttc aaa tta ttc agc aac ctg cgc ccg gca aaa    336
Pro Leu Arg Lys His Phe Lys Leu Phe Ser Asn Leu Arg Pro Ala Lys
            100                 105                 110 ctg tat cag ggg ctg gaa gca ttc tgt ccg ctg cgt gca gac att gcc    384
Leu Tyr Gln Gly Leu Glu Ala Phe Cys Pro Leu Arg Ala Asp Ile Ala
        115                 120                 125 gca aac ggc ttc gac atc ctg tgt gtg cgc gaa ctg acc ggc ggc atc    432
Ala Asn Gly Phe Asp Ile Leu Cys Val Arg Glu Leu Thr Gly Gly Ile
    130                 135                 140 tat ttc ggt cag cca aaa ggc gcg gaa ggt agc gga caa tat gaa aaa    480
Tyr Phe Gly Gln Pro Lys Gly Arg Glu Gly Ser Gly Gln Tyr Glu Lys
145                 150                 155                 160 gcc ttt gat acc gag gtg tat cac cgt ttt gag atc gaa cgt atc gcc    528
Ala Phe Asp Thr Glu Val Tyr His Arg Phe Glu Ile Glu Arg Ile Ala
                165                 170                 175 cgc atc gcg ttt gaa tct gct cgc aag cgt cgc cac aaa gtg acg tcg    576
Arg Ile Ala Phe Glu Ser Ala Arg Lys Arg Arg His Lys Val Thr Ser
            180                 185                 190 atc gat aaa gcc aac gcg ctg caa tcc tct att tta tgg cgg gag atc    624
Ile Asp Lys Ala Asn Ala Leu Gln Ser Ser Ile Leu Trp Arg Glu Ile
        195                 200                 205 gtt aac gag atc gcc acg gaa tac ccg gat gtc gaa ctg gcg cac atg    672
Val Asn Glu Ile Ala Thr Glu Tyr Pro Asp Val Glu Leu Ala His Met
    210                 215                 220 tac atc gac aac gcc acc atg cag ctg att aaa gat cca tca cag ttt    720
Tyr Ile Asp Asn Ala Thr Met Gln Leu Ile Lys Asp Pro Ser Gln Phe
225                 230                 235                 240 gac gtt ctg ctg tgc tcc aac ctg ttt ggc gac att ctg tct gac gag    768
Asp Val Leu Leu Cys Ser Asn Leu Phe Gly Asp Ile Leu Ser Asp Glu
                245                 250                 255 tgc gca atg atc act ggc tcg atg ggg atg ttg cct tcc gcc agc ctg    816
Cys Ala Met Ile Thr Gly Ser Met Gly Met Leu Pro Ser Ala Ser Leu
            260                 265                 270
```

```
aac gag caa ggt ttt gga ctg tat gaa ccg gcg ggc tcg gca cca      864
Asn Glu Gln Gly Phe Gly Leu Tyr Glu Pro Ala Gly Ser Ala Pro
            275                 280                 285 gat atc gca ggc aaa aac atc gcc aac ccg att gca caa atc ctt tcg  912
Asp Ile Ala Gly Lys Asn Ile Ala Asn Pro Ile Ala Gln Ile Leu Ser
290                 295                 300 ctg gca ctg ctg ctg cgt tac agc ctg gat gcc gat gat gcg gct tgc  960
Leu Ala Leu Leu Leu Arg Tyr Ser Leu Asp Ala Asp Asp Ala Ala Cys
305                 310                 315                 320 gcc att gaa cgc gcc att aac cgc gca tta gaa gaa ggc att cgc acc  1008
Ala Ile Glu Arg Ala Ile Asn Arg Ala Leu Glu Glu Gly Ile Arg Thr
                325                 330                 335 ggg gat tta gcc cgt ggc gct gcc gcc gtt agt acc gat gaa atg ggc  1056
Gly Asp Leu Ala Arg Gly Ala Ala Ala Val Ser Thr Asp Glu Met Gly
            340                 345                 350 gat atc att gcc cgc tat gta gca gaa ggg gtg                      1089
Asp Ile Ile Ala Arg Tyr Val Ala Glu Gly Val
            355                 360
```

<210> SEQ ID NO 16
<211> LENGTH: 363
<212> TYPE: PRT
<213> ORGANISM: Artificial Sequence
<220> FEATURE:
<223> OTHER INFORMATION: Synthetic Construct

<400> SEQUENCE: 16

```
Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
                20                  25                  30

Arg Phe Ala Met Arg Ile Thr Thr Ser His Tyr Asp Val Gly Gly Ala
            35                  40                  45

Ala Ile Asp Asn His Gly Gln Pro Leu Pro Pro Ala Thr Val Glu Gly
        50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Gly
                85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
        115                 120                 125

Ala Asn Gly Phe Asp Ile Leu Cys Val Arg Glu Leu Thr Gly Gly Ile
130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg His Lys Val Thr Ser
            180                 185                 190

Ile Asp Lys Ala Asn Ala Leu Gln Ser Ser Ile Leu Trp Arg Glu Ile
        195                 200                 205

Val Asn Glu Ile Ala Thr Glu Tyr Pro Asp Val Glu Leu Ala His Met
210                 215                 220

Tyr Ile Asp Asn Ala Thr Met Gln Leu Ile Lys Asp Pro Ser Gln Phe
225                 230                 235                 240
```

```
Asp Val Leu Leu Cys Ser Asn Leu Phe Gly Asp Ile Leu Ser Asp Glu
            245                 250                 255
Cys Ala Met Ile Thr Gly Ser Met Gly Met Leu Pro Ser Ala Ser Leu
        260                 265                 270
Asn Glu Gln Gly Phe Gly Leu Tyr Glu Pro Ala Gly Gly Ser Ala Pro
            275                 280                 285
Asp Ile Ala Gly Lys Asn Ile Ala Asn Pro Ile Ala Gln Ile Leu Ser
        290                 295                 300
Leu Ala Leu Leu Leu Arg Tyr Ser Leu Asp Ala Asp Asp Ala Ala Cys
305                 310                 315                 320
Ala Ile Glu Arg Ala Ile Asn Arg Ala Leu Glu Glu Gly Ile Arg Thr
                325                 330                 335
Gly Asp Leu Ala Arg Gly Ala Ala Val Ser Thr Asp Glu Met Gly
            340                 345                 350
Asp Ile Ile Ala Arg Tyr Val Ala Glu Gly Val
        355                 360
```

<210> SEQ ID NO 17
<211> LENGTH: 1089
<212> TYPE: DNA
<213> ORGANISM: Artificial Sequence
<220> FEATURE:
<223> OTHER INFORMATION: Synthesized - SEQ ID NO:9 L96G/V198G
<220> FEATURE:
<221> NAME/KEY: CDS
<222> LOCATION: (1)..(1089)
<220> FEATURE:
<221> NAME/KEY: mat_peptide
<222> LOCATION: (1)..(1089)
<220> FEATURE:
<221> NAME/KEY: gene
<222> LOCATION: (1)..(1089)
<223> OTHER INFORMATION: SEQ ID NO:9 L96G/V198G

<400> SEQUENCE: 17

```
atg tcg aag aat tac cat att gcc gta ttg ccg ggg gac ggt att ggt    48
Met Ser Lys Asn Tyr His Ile Ala Val Leu Pro Gly Asp Gly Ile Gly
1               5                   10                  15 ccg gaa gtg atg acc cag gcg ctg aaa gtg ctg gat gcc gtg cgc aac    96
Pro Glu Val Met Thr Gln Ala Leu Lys Val Leu Asp Ala Val Arg Asn
            20                  25                  30 cgc ttt gcg atg cgc atc acc acc agc cat tac gat gta ggc ggc gca   144
Arg Phe Ala Met Arg Ile Thr Thr Ser His Tyr Asp Val Gly Gly Ala
        35                  40                  45 gcc att gat aac cac ggg caa cca ctg ccg cct gcg acg gtt gaa ggt   192
Ala Ile Asp Asn His Gly Gln Pro Leu Pro Pro Ala Thr Val Glu Gly
    50                  55                  60 tgt gag caa gcc gat gcc gtg ctg ttt ggc tcg gta ggc ggc ccg aag   240
Cys Glu Gln Ala Asp Ala Val Leu Phe Gly Ser Val Gly Gly Pro Lys
65                  70                  75                  80 tgg gaa cat tta cca cca gac cag caa cca gaa cgc ggc gcg ctg ggt   288
Trp Glu His Leu Pro Pro Asp Gln Gln Pro Glu Arg Gly Ala Leu Gly
                85                  90                  95 cct ctg cgt aag cac ttc aaa tta ttc agc aac ctg cgc ccg gca aaa   336
Pro Leu Arg Lys His Phe Lys Leu Phe Ser Asn Leu Arg Pro Ala Lys
            100                 105                 110 ctg tat cag ggg ctg gaa gca ttc tgt ccg ctg cgt gca gac att gcc   384
Leu Tyr Gln Gly Leu Glu Ala Phe Cys Pro Leu Arg Ala Asp Ile Ala
        115                 120                 125 gca aac ggc ttc gac atc ctg tgt gtg cgc gaa ctg acc ggc ggc atc   432
Ala Asn Gly Phe Asp Ile Leu Cys Val Arg Glu Leu Thr Gly Gly Ile
```

```
          130                 135                 140
tat ttc ggt cag cca aaa ggc cgc gaa ggt agc gga caa tat gaa aaa      480
Tyr Phe Gly Gln Pro Lys Gly Arg Glu Gly Ser Gly Gln Tyr Glu Lys
145                 150                 155                 160 gcc ttt gat acc gag gtg tat cac cgt ttt gag atc gaa cgt atc gcc      528
Ala Phe Asp Thr Glu Val Tyr His Arg Phe Glu Ile Glu Arg Ile Ala
                165                 170                 175 cgc atc gcg ttt gaa tct gct cgc aag cgt cgc cac aaa gtg acg tcg      576
Arg Ile Ala Phe Glu Ser Ala Arg Lys Arg Arg His Lys Val Thr Ser
            180                 185                 190 atc gat aaa gcc aac ggt ctg caa tcc tct att tta tgg cgg gag atc      624
Ile Asp Lys Ala Asn Gly Leu Gln Ser Ser Ile Leu Trp Arg Glu Ile
        195                 200                 205 gtt aac gag atc gcc acg gaa tac ccg gat gtc gaa ctg gcg cac atg      672
Val Asn Glu Ile Ala Thr Glu Tyr Pro Asp Val Glu Leu Ala His Met
    210                 215                 220 tac atc gac aac gcc acc atg cag ctg att aaa gat cca tca cag ttt      720
Tyr Ile Asp Asn Ala Thr Met Gln Leu Ile Lys Asp Pro Ser Gln Phe
225                 230                 235                 240 gac gtt ctg ctg tgc tcc aac ctg ttt ggc gac att ctg tct gac gag      768
Asp Val Leu Leu Cys Ser Asn Leu Phe Gly Asp Ile Leu Ser Asp Glu
                245                 250                 255 tgc gca atg atc act ggc tcg atg ggg atg ttg cct tcc gcc agc ctg      816
Cys Ala Met Ile Thr Gly Ser Met Gly Met Leu Pro Ser Ala Ser Leu
            260                 265                 270 aac gag caa ggt ttt gga ctg tat gaa ccg gcg ggc ggc tcg gca cca      864
Asn Glu Gln Gly Phe Gly Leu Tyr Glu Pro Ala Gly Gly Ser Ala Pro
        275                 280                 285 gat atc gca ggc aaa aac atc gcc aac ccg att gca caa atc ctt tcg      912
Asp Ile Ala Gly Lys Asn Ile Ala Asn Pro Ile Ala Gln Ile Leu Ser
    290                 295                 300 ctg gca ctg ctg ctg cgt tac agc ctg gat gcc gat gat gcg gct tgc      960
Leu Ala Leu Leu Leu Arg Tyr Ser Leu Asp Ala Asp Asp Ala Ala Cys
305                 310                 315                 320 gcc att gaa cgc gcc att aac cgc gca tta gaa gaa ggc att cgc acc     1008
Ala Ile Glu Arg Ala Ile Asn Arg Ala Leu Glu Glu Gly Ile Arg Thr
                325                 330                 335 ggg gat tta gcc cgt ggc gct gcc gcc gtt agt acc gat gaa atg ggc     1056
Gly Asp Leu Ala Arg Gly Ala Ala Ala Val Ser Thr Asp Glu Met Gly
            340                 345                 350 gat atc att gcc cgc tat gta gca gaa ggg gtg                         1089
Asp Ile Ile Ala Arg Tyr Val Ala Glu Gly Val
        355                 360

<210> SEQ ID NO 18
<211> LENGTH: 363
<212> TYPE: PRT
<213> ORGANISM: Artificial Sequence
<220> FEATURE:
<223> OTHER INFORMATION: Synthetic Construct

<400> SEQUENCE: 18

Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
            20                  25                  30

Arg Phe Ala Met Arg Ile Thr Thr Ser His Tyr Asp Val Gly Gly Ala
        35                  40                  45

Ala Ile Asp Asn His Gly Gln Pro Leu Pro Pro Ala Thr Val Glu Gly
    50                  55                  60
```

Cys Glu Gln Ala Asp Ala Val Leu Phe Gly Ser Val Gly Gly Pro Lys
 65                  70                  75                  80

Trp Glu His Leu Pro Pro Asp Gln Gln Pro Glu Arg Gly Ala Leu Gly
                 85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
        115                 120                 125

Ala Asn Gly Phe Asp Ile Leu Cys Val Arg Glu Leu Thr Gly Gly Ile
    130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg His Lys Val Thr Ser
            180                 185                 190

Ile Asp Lys Ala Asn Gly Leu Gln Ser Ser Ile Leu Trp Arg Glu Ile
        195                 200                 205

Val Asn Glu Ile Ala Thr Glu Tyr Pro Asp Val Glu Leu Ala His Met
    210                 215                 220

Tyr Ile Asp Asn Ala Thr Met Gln Leu Ile Lys Asp Pro Ser Gln Phe
225                 230                 235                 240

Asp Val Leu Leu Cys Ser Asn Leu Phe Gly Asp Ile Leu Ser Asp Glu
                245                 250                 255

Cys Ala Met Ile Thr Gly Ser Met Gly Met Leu Pro Ser Ala Ser Leu
            260                 265                 270

Asn Glu Gln Gly Phe Gly Leu Tyr Glu Pro Ala Gly Gly Ser Ala Pro
        275                 280                 285

Asp Ile Ala Gly Lys Asn Ile Ala Asn Pro Ile Ala Gln Ile Leu Ser
    290                 295                 300

Leu Ala Leu Leu Leu Arg Tyr Ser Leu Asp Ala Asp Asp Ala Ala Cys
305                 310                 315                 320

Ala Ile Glu Arg Ala Ile Asn Arg Ala Leu Glu Glu Gly Ile Arg Thr
                325                 330                 335

Gly Asp Leu Ala Arg Gly Ala Ala Val Ser Thr Asp Glu Met Gly
            340                 345                 350

Asp Ile Ile Ala Arg Tyr Val Ala Glu Gly Val
        355                 360

<210> SEQ ID NO 19
<211> LENGTH: 1089
<212> TYPE: DNA
<213> ORGANISM: Artificial Sequence
<220> FEATURE:
<223> OTHER INFORMATION: Synthesized - SEQ ID NO:10 L96V/V198G
<220> FEATURE:
<221> NAME/KEY: CDS
<222> LOCATION: (1)..(1089)
<220> FEATURE:
<221> NAME/KEY: mat_peptide
<222> LOCATION: (1)..(1089)
<220> FEATURE:
<221> NAME/KEY: gene
<222> LOCATION: (1)..(1089)
<223> OTHER INFORMATION: SEQ ID NO:10 L96V/V198G

<400> SEQUENCE: 19 atg tcg aag aat tac cat att gcc gta ttg ccg ggg gac ggt att ggt     48

```
        Met Ser Lys Asn Tyr His Ile Ala Val Leu Pro Gly Asp Gly Ile Gly
        1               5                   10                  15 ccg gaa gtg atg acc cag gcg ctg aaa gtg ctg gat gcc gtg cgc aac            96
Pro Glu Val Met Thr Gln Ala Leu Lys Val Leu Asp Ala Val Arg Asn
                20                  25                  30 cgc ttt gcg atg cgc atc acc acc agc cat tac gat gta ggc ggc gca           144
Arg Phe Ala Met Arg Ile Thr Thr Ser His Tyr Asp Val Gly Gly Ala
            35                  40                  45 gcc att gat aac cac ggg caa cca ctg ccg cct gcg acg gtt gaa ggt           192
Ala Ile Asp Asn His Gly Gln Pro Leu Pro Pro Ala Thr Val Glu Gly
        50                  55                  60 tgt gag caa gcc gat gcc gtg ctg ttt ggc tcg gta ggc ggc ccg aag           240
Cys Glu Gln Ala Asp Ala Val Leu Phe Gly Ser Val Gly Gly Pro Lys
65                  70                  75                  80 tgg gaa cat tta cca cca gac cag caa cca gaa cgc ggc gcg ctg gtg           288
Trp Glu His Leu Pro Pro Asp Gln Gln Pro Glu Arg Gly Ala Leu Val
                85                  90                  95 cct ctg cgt aag cac ttc aaa tta ttc agc aac ctg cgc ccg gca aaa           336
Pro Leu Arg Lys His Phe Lys Leu Phe Ser Asn Leu Arg Pro Ala Lys
            100                 105                 110 ctg tat cag ggg ctg gaa gca ttc tgt ccg ctg cgt gca gac att gcc           384
Leu Tyr Gln Gly Leu Glu Ala Phe Cys Pro Leu Arg Ala Asp Ile Ala
        115                 120                 125 gca aac ggc ttc gac atc ctg tgt gtg cgc gaa ctg acc ggc ggc atc           432
Ala Asn Gly Phe Asp Ile Leu Cys Val Arg Glu Leu Thr Gly Gly Ile
130                 135                 140 tat ttc ggt cag cca aaa ggc cgc gaa ggt agc gga caa tat gaa aaa           480
Tyr Phe Gly Gln Pro Lys Gly Arg Glu Gly Ser Gly Gln Tyr Glu Lys
145                 150                 155                 160 gcc ttt gat acc gag gtg tat cac cgt ttt gag atc gaa cgt atc gcc           528
Ala Phe Asp Thr Glu Val Tyr His Arg Phe Glu Ile Glu Arg Ile Ala
                165                 170                 175 cgc atc gcg ttt gaa tct gct cgc aag cgt cgc cac aaa gtg acg tcg           576
Arg Ile Ala Phe Glu Ser Ala Arg Lys Arg Arg His Lys Val Thr Ser
            180                 185                 190 atc gat aaa gcc aac ggt ctg caa tcc tct att tta tgg cgg gag atc           624
Ile Asp Lys Ala Asn Gly Leu Gln Ser Ser Ile Leu Trp Arg Glu Ile
        195                 200                 205 gtt aac gag atc gcc acg gaa tac ccg gat gtc gaa ctg gcg cac atg           672
Val Asn Glu Ile Ala Thr Glu Tyr Pro Asp Val Glu Leu Ala His Met
210                 215                 220 tac atc gac aac gcc acc atg cag ctg att aaa gat cca tca cag ttt           720
Tyr Ile Asp Asn Ala Thr Met Gln Leu Ile Lys Asp Pro Ser Gln Phe
225                 230                 235                 240 gac gtt ctg ctg tgc tcc aac ctg ttt ggc gac att ctg tct gac gag           768
Asp Val Leu Leu Cys Ser Asn Leu Phe Gly Asp Ile Leu Ser Asp Glu
                245                 250                 255 tgc gca atg atc act ggc tcg atg ggg atg ttg cct tcc gcc agc ctg           816
Cys Ala Met Ile Thr Gly Ser Met Gly Met Leu Pro Ser Ala Ser Leu
            260                 265                 270 aac gag caa ggt ttt gga ctg tat gaa ccg gcg ggc ggc tcg gca cca           864
Asn Glu Gln Gly Phe Gly Leu Tyr Glu Pro Ala Gly Gly Ser Ala Pro
        275                 280                 285 gat atc gca ggc aaa aac atc gcc aac ccg att gca caa atc ctt tcg           912
Asp Ile Ala Gly Lys Asn Ile Ala Asn Pro Ile Ala Gln Ile Leu Ser
290                 295                 300 ctg gca ctg ctg ctg cgt tac agc ctg gat gcc gat gat gcg gct tgc           960
Leu Ala Leu Leu Leu Arg Tyr Ser Leu Asp Ala Asp Asp Ala Ala Cys
305                 310                 315                 320
```

```
gcc att gaa cgc gcc att aac cgc gca tta gaa gaa ggc att cgc acc        1008
Ala Ile Glu Arg Ala Ile Asn Arg Ala Leu Glu Glu Gly Ile Arg Thr
            325                 330                 335 ggg gat tta gcc cgt ggc gct gcc gcc gtt agt acc gat gaa atg ggc        1056
Gly Asp Leu Ala Arg Gly Ala Ala Ala Val Ser Thr Asp Glu Met Gly
        340                 345                 350 gat atc att gcc cgc tat gta gca gaa ggg gtg                            1089
Asp Ile Ile Ala Arg Tyr Val Ala Glu Gly Val
            355                 360
```

<210> SEQ ID NO 20
<211> LENGTH: 363
<212> TYPE: PRT
<213> ORGANISM: Artificial Sequence
<220> FEATURE:
<223> OTHER INFORMATION: Synthetic Construct

<400> SEQUENCE: 20

```
Met Ser Lys Asn Tyr His Ile Ala Val Leu Pro Gly Asp Gly Ile Gly
1               5                   10                  15

Pro Glu Val Met Thr Gln Ala Leu Lys Val Leu Asp Ala Val Arg Asn
            20                  25                  30

Arg Phe Ala Met Arg Ile Thr Thr Ser His Tyr Asp Val Gly Gly Ala
        35                  40                  45

Ala Ile Asp Asn His Gly Gln Pro Leu Pro Pro Ala Thr Val Glu Gly
    50                  55                  60

Cys Glu Gln Ala Asp Ala Val Leu Phe Gly Ser Val Gly Gly Pro Lys
65                  70                  75                  80

Trp Glu His Leu Pro Pro Asp Gln Gln Pro Glu Arg Gly Ala Leu Val
                85                  90                  95

Pro Leu Arg Lys His Phe Lys Leu Phe Ser Asn Leu Arg Pro Ala Lys
            100                 105                 110

Leu Tyr Gln Gly Leu Glu Ala Phe Cys Pro Leu Arg Ala Asp Ile Ala
        115                 120                 125

Ala Asn Gly Phe Asp Ile Leu Cys Val Arg Glu Leu Thr Gly Gly Ile
    130                 135                 140

Tyr Phe Gly Gln Pro Lys Gly Arg Glu Gly Ser Gly Gln Tyr Glu Lys
145                 150                 155                 160

Ala Phe Asp Thr Glu Val Tyr His Arg Phe Glu Ile Glu Arg Ile Ala
                165                 170                 175

Arg Ile Ala Phe Glu Ser Ala Arg Lys Arg His Lys Val Thr Ser
            180                 185                 190

Ile Asp Lys Ala Asn Gly Leu Gln Ser Ser Ile Leu Trp Arg Glu Ile
        195                 200                 205

Val Asn Glu Ile Ala Thr Glu Tyr Pro Asp Val Glu Leu Ala His Met
    210                 215                 220

Tyr Ile Asp Asn Ala Thr Met Gln Leu Ile Lys Asp Pro Ser Gln Phe
225                 230                 235                 240

Asp Val Leu Leu Cys Ser Asn Leu Phe Gly Asp Ile Leu Ser Asp Glu
                245                 250                 255

Cys Ala Met Ile Thr Gly Ser Met Gly Met Leu Pro Ser Ala Ser Leu
            260                 265                 270

Asn Glu Gln Gly Phe Gly Leu Tyr Glu Pro Ala Gly Gly Ser Ala Pro
        275                 280                 285

Asp Ile Ala Gly Lys Asn Ile Ala Asn Pro Ile Ala Gln Ile Leu Ser
    290                 295                 300
```

-continued

```
Leu Ala Leu Leu Leu Arg Tyr Ser Leu Asp Ala Asp Asp Ala Ala Cys
305                 310                 315                 320

Ala Ile Glu Arg Ala Ile Asn Arg Ala Leu Glu Glu Gly Ile Arg Thr
            325                 330                 335

Gly Asp Leu Ala Arg Gly Ala Ala Ala Val Ser Thr Asp Glu Met Gly
            340                 345                 350

Asp Ile Ile Ala Arg Tyr Val Ala Glu Gly Val
            355                 360
```